US007301037B2

(12) United States Patent
Ge et al.

(10) Patent No.: US 7,301,037 B2
(45) Date of Patent: Nov. 27, 2007

(54) CHARGED COMPOUNDS COMPRISING A NUCLEIC ACID BINDING MOIETY AND USES THEREFOR

(75) Inventors: Yigong Ge, So. San Francisco, CA (US); Matthew J. Taylor, San Francisco, CA (US); Eldon E. Baird, Half Moon Bay, CA (US); Heinz E. Moser, San Mateo, CA (US); Roland W. Burli, San Francisco, CA (US)

(73) Assignee: Genesoft, Inc., South San Francisco, CA (US)

( * ) Notice: Subject to any disclaimer, the term of this patent is extended or adjusted under 35 U.S.C. 154(b) by 0 days.

(21) Appl. No.: 11/487,164

(22) Filed: Jul. 14, 2006

(65) Prior Publication Data

US 2007/0105135 A1 May 10, 2007

Related U.S. Application Data

(60) Continuation of application No. 10/278,870, filed on Oct. 22, 2002, now Pat. No. 7,078,536, which is a division of application No. 09/808,729, filed on Mar. 14, 2001, now Pat. No. 6,555,693.

(60) Provisional application No. 60/189,930, filed on Mar. 16, 2000.

(51) Int. Cl.
*C07D 209/56* (2006.01)
*C07D 409/00* (2006.01)
*C07D 413/00* (2006.01)
*A01N 57/18* (2006.01)
*A01N 43/06* (2006.01)
*A01N 43/36* (2006.01)
*A61K 31/535* (2006.01)

(52) U.S. Cl. ................ 548/527; 514/422; 514/444; 514/141; 514/232.8; 549/59; 544/141

(58) Field of Classification Search ............... 548/527; 514/141, 232.8, 422, 444; 544/141; 549/59
See application file for complete search history.

(56) References Cited

U.S. PATENT DOCUMENTS

| 4,738,980 A | 4/1988 | Arcamone et al. |
| 4,766,142 A | 8/1988 | Arcamone et al. |
| 4,912,199 A | 3/1990 | Lown et al. |
| 5,017,599 A | 5/1991 | Lazzari et al. |
| 5,049,579 A | 9/1991 | Lazzari et al. |
| 5,310,752 A | 5/1994 | Lazzari et al. |
| 5,472,976 A | 12/1995 | Animati et al. |
| 5,502,068 A | 3/1996 | Lown et al. |
| 5,616,606 A | 4/1997 | Lown et al. |
| 5,670,534 A | 9/1997 | Animati et al. |
| 5,698,674 A | 12/1997 | Bruice et al. |
| 5,753,629 A | 5/1998 | Beria et al. |
| 5,801,155 A | 9/1998 | Kutyavin et al. |
| 5,852,011 A | 12/1998 | Matsunaga et al. |
| 6,090,947 A | 7/2000 | Dervan et al. |
| 6,555,693 B2* | 4/2003 | Ge et al. ............... 544/368 |

FOREIGN PATENT DOCUMENTS

| GB | 2310207 | 2/1996 |
| WO | WO 92/13838 | 8/1992 |
| WO | WO 93/13739 | 7/1993 |
| WO | WO 94/20463 | 9/1994 |
| WO | 98/50582 | 7/1997 |
| WO | WO 98/37066 | 8/1998 |
| WO | WO 98/37067 | 8/1998 |
| WO | WO 98/37087 | 8/1998 |
| WO | WO 98/45284 | 10/1998 |
| WO | WO 98/49142 | 11/1998 |
| WO | WO 98/52614 | 11/1998 |
| WO | WO 99/27939 | 6/1999 |
| WO | WO 99/41367 | 8/1999 |
| WO | WO 99/50265 | 10/1999 |
| WO | 99/62890 | 12/1999 |
| WO | WO 99/64413 | 12/1999 |
| WO | WO 00/40605 | 7/2000 |

OTHER PUBLICATIONS

Baird et al., "Solid Phase Synthesis of Polyamides Containing Imidazole and Pyrrole Amino Acids," *J. Am. Chem. Soc.*, 118:6141-6146 (1996).
Arcamone et al., "Synthesis, DNA binding and antiviral activity of distamycin analogues containing different heterocyclic moieties," *Anti-Cancer Drug Design*, 1:235-244 (1986).
El-Naggaar et al., "Synthesis of Some 2-Thenoyl-, 5-Bromo-2-thenoyl- and 5-Nitro-2-thenoylamino Acid Derivatives and their Antimicrobial Activity," *J. Indian Chem. Soc.*, LIX:783-786 (1982).
Sharma et al., "Design and Synthesis of Novel Thiazole-Containing Cross-Linked Polyamides Related to the Antiviral Antibiotic Distamycin," *J. Org. Chem*, page est: 5.3 (1999).
Plouvier et al., "DNA-sequence specific recognition by a thiazole analogue of netropsin: a comparative footprinting study," *Nucleic Acids Research*, 19(21):5821-5829 (1991).

(Continued)

*Primary Examiner*—Jezia Riley
(74) *Attorney, Agent, or Firm*—Townsend and Townsend and Crew LLP

(57) ABSTRACT

Charged compounds are provided that comprise one or more regions of localized positive charge, compositions comprising such compounds, methods of synthesizing such compounds, methods of screening such compounds to identify those having anti-infective activity, and methods of using such compounds to prevent or inhibit infections. These compounds, and compositions containing them, have multiple applications, including use in human and animal medicine and in agriculture.

11 Claims, No Drawings

OTHER PUBLICATIONS

Kopka et al., "Defining GC-specificity in the minor groove: side-by-side binding of the di-imidazole lexitropsin to C-A-T-G-G-C-C-A-T-G," *Structure*, 5(8):1033-1046 (1997).

Rao et al., "Molecular recognition between oligopeptides and nucleic acids: DNA sequence specificity and binding properties of thiazole-lexitropsins incorporating the concepts of base site acceptance and avoidance," *Anti-Cancer Drug Design*, 5:3-20 (1990).

Zakrzewska et al., "Theoretical Study of the Sequence Selectivity of Isolexins, Isohelical DNA Groove Binding Ligands. Proposal for the GC Minor Groove Specific Compounds," *Journal of Biomolecular Structure & Dynamics*, ISSN 0739-1102, 5(5):1043-1058 (1988).

Bailly et al., "Sequence-Specific DNA Minor Groove Binders. Design and Synthesis of Netropsin and Distamycin Analogues," *Bioconjugate Chemistry*, 9(5):513-538 (1998).

Nielsen, "Sequence-Selective DNA Recognition by Synthetic Ligands," *Bioconjugate Chemistry*, 2(1):1-12 (1991).

Vaquero et al., "Small ligands that neither bind to nor alter the structure of d(GA•TC)n sequences in DNA," *FEBS Letters*, 420:156-160 (1997).

Matsumoto et al., "Synthesis of Sulfonamido Oligo-*N*-Methylpyrrole-Carboxamide Derivatives and Their Photochemical DNA Cleaving Activities," *Heterocycles*, 33(1):135-138 (1992).

Berg, S.M. et al., "Pharmaceutical Salts", *Journal of Pharmaceutical Science*, 66, 1-19 (1977).

Ae NimPae et al., "Synthesis and In Vitro Activity of New Oxazolidinone Antibacterial Agents Having Substituted Isoxazoles", *Bioorganic & Medicinal Chemistry Letters* 9 (1999) 1679-2684.

Chu-Biao Xue et al, "Synthesis and Antiplatelet Effects of An Isoxazole Series of Glycoprotein Iib/Iiia Antagonists", *Bioorganic & Medicinal Chemistry Letters*, Letters 8 (1998) 3499-3504.

D. Chiarino et al., "Synthesis of New Isoxazole Aminoalcohols", *J. Heterocyclic Chem.* 25:(1) pp. 337-342 (1988) XP002041517.

Steven P. Tanis and David B. Head, "Furans in Synthesis. The Preparation of (+)-Lactaral", *Tetrahedron Letters*, 23:(52) pp. 5509-5512 (1982) XP002208603.

Pier Giovanni Baraldi et al., "Synthesis of 3-Substituted-7-alkoxy-5H-pyrazolo '4, 3-dl-1,2,3-triazin-4(3H)-ones" *Synthesis*, pp. 1437-1440, (1994), XP002208604.

Thomas C. Bruice et al., "Rational design of substituted tripyrrole peptides that complex with DNA by both selective minor-groove binding and electrostatic interaction with the phosphate backbone", *Proc. Natl. Acad. Sci*, 89: pp. 1700-1704 (Mar. 1992).

* cited by examiner

CHARGED COMPOUNDS COMPRISING A NUCLEIC ACID BINDING MOIETY AND USES THEREFOR

CROSS REFERENCES TO RELATED APPLICATIONS

This application is a continuation of U.S. Ser. No. 10/278,870, filed Oct. 22, 2002 now U.S. Pat. No. 7,078,536, which is a divisional of U.S. Ser. No. 09/808,729, filed Mar. 14, 2001 now U.S. Pat. No. 6,555,693 which claims the benefit of provisional applications U.S. Ser. No. 60/189,930, filed Mar. 16, 2000, the disclosures of each of the above being incorporated herein by reference.

STATEMENT AS TO RIGHTS TO INVENTIONS MADE UNDER FEDERALLY SPONSORED RESEARCH AND DEVELOPMENT

The United States government may have certain rights to this invention pursuant to DARPA grant no. N65236-99-1-5427.

REFERENCE TO A "SEQUENCE LISTING," A TABLE, OR A COMPUTER PROGRAM LISTING APPENDIX SUBMITTED ON A COMPACT DISK.

BACKGROUND OF THE INVENTION

Many compounds, either naturally occurring or synthetic, have been found to bind to double stranded nucleic acid, especially double stranded deoxyribonucleic acid ("dsDNA"). Depending on their structure, the compounds bind to different parts of the nucleic acid. Some bind to the major groove while others associate with the minor groove. Still others intercalate between adjacent base pairs. Combination binding modes are also known, in which a compound has binding interactions with more than one site in the nucleic acid.

Certain dsDNA binding compounds may be used to regulate the expression of genes for medical purposes. If a disease is characterized by the overexpression or the undesired expression of a gene (e.g., an oncogene), the disease may be treated by suppressing in toto or in part the expression of the gene by the binding of such compounds to the gene or a promoter site thereof. Infections by pathogens such fungi, bacteria, and viruses may be combated with compounds that affect the expression of genes essential for the proliferation of the pathogen.

Whatever the application, the compound must strongly bind to dsDNA, generally meaning that it binds with an association constant of at least $10^6$ $M^{-1}$, preferably at least about $10^9$ $M^{-1}$. However, binding strength alone is not determinative of efficacy. Many other factors come into play, including, for instance, cellular uptake, stability, toxicity, binding specificity, and the like. A compound that is acceptable or superior in one characteristic may be fatally deficient in another characteristic. Thus, there is a continuing need to develop new classes of nucleic acid binding compounds for use in such applications.

BRIEF SUMMARY OF THE INVENTION

The present invention provides a new class of compounds, as well as compositions comprising such compounds, methods of synthesizing such compounds, methods of screening such compounds to identify those having anti-infective activity, and methods of using such compounds to prevent or inhibit infections.

In one aspect, the invention provides a class of charged compounds. The members of this class of compounds each comprise a nucleic acid binding moiety, and can be represented by formula (I):

W—Y-[Het]-L-[NABM]   (I)

or a salt thereof, preferably a pharmaceutically acceptable salt. Additionally, esters, amides, prodrugs, isomers, or metabolites of formula I are also within the scope of the present invention.

With respect to this invention, "NABM" refers to nucleic acid binding moiety, particularly nucleic acid binding moieties that bind to or associate with double-stranded nucleic acids, particularly dsDNA. NABMs include small molecules, proteins, and nucleic acids. Preferred small molecules include polyamides, particularly synthetic polyamides, and preferred nucleic acids include oligonucleotides. NABMs include intercalating moieties, minor groove binding moieties, major groove binding moieties, and those that include moieties that bind in a combination of such modes, e.g., an NABM that includes both minor and major groove binding moieties.

In formula I above, an NABM is linked to a heteroaromatic moiety ("Het") via linker "L". L represents a bond, preferably a covalent bond, or a linking group. Het represents a heteroaromatic moiety other than N-methyl or N-hydrogen pyrrole, selected from the group consisting of

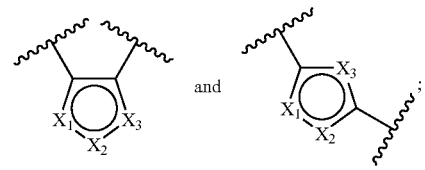

wherein one of $X_1$, $X_2$, and $X_3$ is a ring vertex selected from the group consisting of —O—, —S—, and —$NR_3$—, and the other two of $X_1$, $X_2$, and $X_3$ are ring vertices selected from the group consisting of =N— and =$CR_4$—.

Covalently attached to the heteroaromatic moiety [Het] is a substituent having the formula:

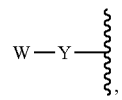

wherein Y is selected from O, S, S(O), $SO_2$, $C(R_1)_2$, $N(R_3)SO_2$, $SO_2N(R_3)$ and $NR_3$; and W is halogen or a group having the formula:

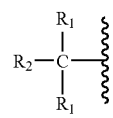

The various R groups in formula I have the following meanings: each $R_1$ is independently selected from H, F, substituted or unsubstituted (C₁-C₆)alkyl and a substituted or unsubstituted (C₁-C₆)heteroalkyl group; R₂ is a moiety bearing a polar group if Y is other than NR₃ and is a moiety bearing a polar group, a substituted or unsubstituted (C₁-C₁₂)alkyl group or a substituted or unsubstituted (C₁-C₁₂) heteroalkyl group if Y is NR₃; each R₃ is independently selected from H, a substituted or unsubstituted (C₁-C₁₂)alkyl group and a substituted or unsubstituted (C₁-C₁₂)heteroalkyl group, provided that neither of R₂(R₁)₂C and R₃ contains a 2-chloroethyl or 2-hydroxyethyl group when Y equals NR₃; and each R₄ is independently selected from hydrogen, halogen, an amino group, a (C₁-C₈)alkylamino group, a di(C₁-C₈)alkylamino group, a tri(C₁-C₈)alkyl ammonium group, a hydroxyl group, a (C₁-C₈)alkoxy group, a thiol group, a (C₁-C₈)thioether group, a (C₁-C₈)sulfone group, a (C₁-C₈) sulfoxide group, a (C₁-C₈)sulfonamide group, a substituted or unsubstituted (C₁-C₁₂)alkyl group and a substituted or unsubstituted (C₁-C₁₂)heteroalkyl group.

Additionally, at least one of R₂, [Het], or [NABM] has a positive charge.

In one group of preferred embodiments, the compounds of the invention can be represented by formula (Ia)

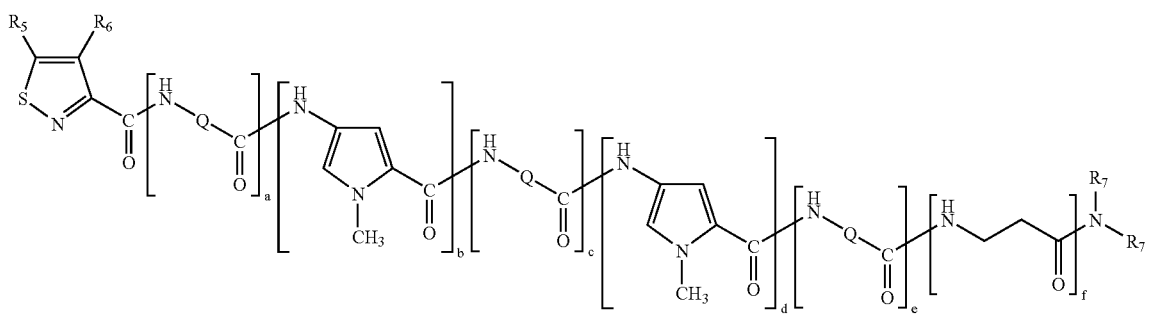

(Ia)

or a salt, preferably a phalgaceutically acceptable salt, or an ester, amide, prodrug, isomer, or metabolite thereof.

In formula Ia, the subscripts a, b, and d are each independently 0, 1, 2, 3, 4, or 5, with the proviso that at least one of a, b, or d is other than 0. The subscripts c, e and f are each independently 0 or 1.

In these embodiments, R₅ is selected from halogen, OR₇ and N(R₇)₂. R₆ is selected from hydrogen, halogen, a substituted or unsubstituted (C₁-C₁₂)alkyl group and a substituted or unsubstituted (C₁-C₁₂)heteroalkyl group. Each R₇ is independently selected from hydrogen, a substituted or unsubstituted (C₁-C₁₂)allyl group and a substituted or unsubstituted (C₁-C₁₂)heteroalkyl group. Each Q is independently selected from —(CH₂)₂—, —(CH₂)₃—, and a heteroaromatic ring independently selected from the group consisting of substituted or unsubstituted imidazole, pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,2,4-oxadiazole, 1,3,4-oxadiazole, and thiophene rings. Preferably, Q is a thiophene ring. Exemplary suitable substituents in a heteroaromatic ring Q include Cl, F, CH₃, and hydroxy.

Compounds according to the invention can be in unpurified, substantially purified, and purified forms. The compounds can be present with any additional component(s) such as a solvent, reactant, or by-product that is present during compound synthesis or purification, and any additional component(s) that is present during the use or manufacture of a compound or that is added during formulation or compounding of a compound.

In another aspect, the present invention provides methods for synthesizing the compounds of the invention. Broadly, such methods comprise linking a NABM to R₂(R₁)₂C—Y-[Het], either directly or through an optional linking group L. The various moieties of the invention can be synthetic or natural products. Synthetic moieties may be synthesized by solution or solid phase methods. Two or moieties may also be synthesized together.

In yet another aspect, the invention provides compositions comprising a compound according to the invention and one or more excipients, diluents, or carriers. Such compositions can be dry or liquid formulations. The particular composition employed will depend on the intended application for the compound. Compounds according to this invention have been found to be strongly bind dsDNA. Preferably, the association constant for a compound of the invention an dsDNA is at least about $10^6$ M$^{-1}$, more preferably at least about $10^9$ M$^{-1}$, and most preferably about $10^{10}$ M$^{-1}$, $10^{11}$ M$^{-1}$, $10^{12}$ M$^{-1}$ or more. Some compositions have been found to be effective in inhibiting the proliferation of pathogens such as fungi and bacteria.

Applications for the compounds and compositions of the invention include anti-infective uses. Such uses can be prophylactic or therapeutic in nature. These uses are accomplished by contacting a pathogen of a eukaryotic organism with an amount of a compound of the invention sufficient to achieve the desired result. Contacting can occur in vitro or in vivo, as the context requires. Preferred embodiments of this aspect involve inhibiting the proliferation of a pathogenic organism. Inhibition can be achieved by killing the organism, by reducing its rate of proliferation, or by reducing or eliminating a pathogenic aspect of the organism, for example, by inhibiting expression of a pathogenic gene (e.g., a gene encoding a toxin). Representative pathogens that can be affected by the preventative and therapeutic methods of the invention include eukaryotic and prokaryotic organisms, as well as viruses. Preferred targets are bacteria and fungi.

The treatment-related aspect of this invention is directed to both animals and plants that serve as hosts, or intermediaries, for the targeted pathogen. As such, the invention has implications in animal health and medicine as well as in agriculture.

In yet another aspect, the invention provides methods of screening to identify compounds of the invention that have anti-infective activity. These screening methods include both in vitro and in vivo screening methods, and can include methods involving an in vitro screen followed by an in vivo screen (e.g., a cell-based screen). In either format, the methods are preferably high throughput methods, meaning that more than about 10, preferably, more than about 100, 1,000, or 10,000 compounds are screened at once. In each of the above recitations, a "charged compound" refers to compounds that are positively charged under assay or physiological conditions, which are typically neutral or slightly acidic (pH about 5 to about 7). Many compounds are illustrated as having amine components in their neutral form. Nevertheless, one of skill in the art will appreciate that these amines can carry a positive charge (e.g., be protonated) at physiological pH or under typical assay conditions.

These and other aspects and embodiments of the invention are described further in the following detailed description.

BRIEF DESCRIPTION OF THE DRAWINGS

Not applicable

DETAILED DESCRIPTION OF THE INVENTION

Abbreviations and Definitions

The term "alkyl," by itself or as part of another substituent, means, unless otherwise stated, a straight or branched chain, or cyclic hydrocarbon radical, or combination thereof, which may be fully saturated, mono- or polyunsaturated and can include di- and multivalent radicals, having the number of carbon atoms designated (i.e. $C_1$-$C_{10}$ means one to ten carbons). Examples of saturated hydrocarbon radicals include groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

The term "alkylene" by itself or as part of another substituent means a divalent radical derived from an alkane, as exemplified by —$CH_2CH_2CH_2CH_2$—. Typically, an alkyl (or alkylene) group will have from 1 to 24 carbon atoms, with those groups having 10 or fewer carbon atoms being preferred in the present invention. A "lower alkyl" or "lower alkylene" is a shorter chain alkyl or alkylene group, generally having six or fewer carbon atoms.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a stable straight or branched chain, or cyclic hydrocarbon radical, or combinations thereof, consisting of the stated number of carbon atoms and from one to three heteroatoms selected from the group consisting of O, N, Si and S, and wherein the nitrogen and sulfur atoms may optionally be oxidized and the nitrogen heteroatom may optionally be quaternized. The heteroatom(s) O, N and S may be placed at any interior position of the heteroalkyl group. The heteroatom Si may be placed at any position of the heteroalkyl group, including the position at which the alkyl group is attached to the remainder of the molecule. Examples include —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—OCH$_3$, and —CH=CH—N($CH_3$)—$CH_3$. Up to two heteroatoms may be consecutive, such as, for example, —$CH_2$—NH—OCH$_3$ and —$CH_2$—Si($CH_3$)$_3$. Similarly, the term "heteroalkylene" by itself or as part of another substituent means a divalent radical derived from heteroalkyl, as exemplified by —$CH_2$—$CH_2$—S—$CH_2CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include cyclopentyl, cyclohexyl, 1-cyclohexenyl, 3-cyclohexenyl, cycloheptyl, and the like. Examples of heterocycloalkyl include 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is mean to include trifluoromethyl, 2,2,2-trifluoroethyl, 4-chlorobutyl, 3-bromopropyl, and the like.

The term "aryl" means, unless otherwise stated, a polyunsaturated, typically aromatic, hydrocarbon substituent which can be a single ring or multiple rings (up to three rings) which are fused together or linked covalently. The term "heteroaryl" refers to aryl groups (or rings) that contain from zero to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") are meant to include both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be a variety of groups selected from: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NH—C(NH$_2$)=NH, —NR'C(NH$_2$)=NH, —NH—C(NH$_2$)=NR', —S(O)R', —S(O)$_2$R', —S(O)$_2$NR'R", —CN and —NO$_2$ in a number ranging from zero to (2m'+1), where m is the total number of carbon atoms in such radical. R', R" and R'" each independently refer to hydrogen, unsubstituted (C$_1$-C$_8$)alkyl and heteroalkyl, unsubstituted aryl, aryl substituted with 1-3 halogens, unsubstituted alkyl, alkoxy or thioalkoxy groups, or aryl-(C$_1$-C$_4$)alkyl groups. When R' and R" are attached to the same nitrogen atom, they can be combined with the nitrogen atom to form a 5-, 6-, or 7-membered ring. For example, —NR'R" is meant to include 1-pyrrolidinyl and 4-morpholinyl. From the above discussion of substituents, one of skill in the art will understand that the term "alkyl" is meant to include groups such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like). Preferably, the substituted alkyl and heteroalkyl groups have from 1 to 4 substituents, more preferably 1, 2 or 3 substituents. Exceptions are those perhalo alkyl groups (e.g., pentafluoroethyl and the like) which are also preferred and contemplated by the present invention.

Similarly, substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O)NR'R", —NR"C(O)R', —NR"C(O)$_2$R', ,—NR'—C(O)NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system; and where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.

Two of the substituents on adjacent atoms of the aryl or heteroaryl ring may optionally be replaced with a substituent of the formula -T-C(O)—(CH$_2$)$_q$—U—, wherein T and U are independently —NH—, —O—, —CH$_2$— or a single bond, and q is an integer of from 0 to 2. Alternatively, two of the substituents on adjacent atoms of the aryl or heteroaryl ring may optionally be replaced with a substituent of the formula -A-(CH$_2$)$_r$-B—, wherein A and B are independently —CH$_2$—, —O—, —NH—, —S—, —S(O)—, —S(O)$_2$—, —S(O)$_2$NR'— or a single bond, and r is an integer of from 1 to 3. One of the single bonds of the new ring so formed may optionally be replaced with a double bond. Alternatively, two of the substituents on adjacent atoms of the aryl or heteroaryl ring may optionally be replaced with a substituent of the formula —(CH$_2$)$_s$—X—(CH$_2$)$_t$—, where s and t are independently integers of from 0 to 3, and X is —O—, —NR'—, —S—, —S(O)—, —S(O)$_2$—, or —S(O)$_2$NR'—. The substituent R' in —NR'— and —S(O)$_2$NR'— is selected from hydrogen or unsubstituted (C$_1$-C$_6$)alkyl.

As used herein, the term "heteroatom" is meant to include oxygen (O), nitrogen (N), sulfur (S) and silicon (Si).

The term "pharmaceutically acceptable salts" is meant to include salts of the active compounds which are prepared with relatively nontoxic acids or bases, depending on the particular substituents found on the compounds described herein. When compounds of the present invention contain relatively acidic ftmctionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulftiric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge, S. M., et al, "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

In addition to salt forms, the present invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

Certain compounds of the present invention can exist in unsolvated forms as well as solvated forms, including hydrated forms. In general, the solvated forms are equivalent to unsolvated forms and are intended to be encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are all intended to be encompassed within the scope of the present invention.

The compounds of the present invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are intended to be encompassed within the scope of the present invention.

In the discussions below, reference is made to dsDNA as the nucleic acid, but it is to be understood that the invention is not limited to dsDNA and is applicable to other nucleic acids, i.e., ribonucleic acid.

Compounds.

Nucleic acid binding compounds of this invention represented by formula (I) (reproduced below for convenience)

W—Y-[Het]-L-[NABM]    (I)

are now discussed in greater detail, especially with reference to preferred embodiments thereof.

As noted above, [NABM] is a double-stranded nucleic acid binding moiety; L is a covalent bond or a linking group; [Het] is a heteroaromatic moiety other than N-methyl or N-hydrogen pyrrole, selected from:

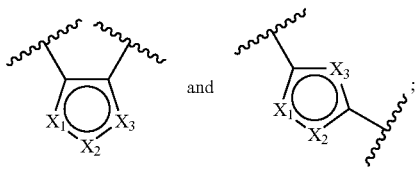

wherein one of $X_1$, $X_2$, and $X_3$ is a ring vertex selected from —O—, —S—, and —$NR_3$—, and the other two of $X_1$, $X_2$, and $X_3$ are ring vertices selected from =N— and =$CR_4$—. Additionally, the circle in the five-membered ring above is meant to indicate the presence of two double bonds, which, in some embodiments, can move within the ring.

Returning to formula I, the letter Y represents O, S, S(O), $SO_2$, $C(R_1)_2$, $N(R_3)SO_2$, $SO_2N(R_3)$, or $NR_3$. The letter W represents a halogen atom of a group having the formula:

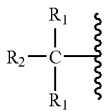

The various R groups have the following meanings: each $R_1$ is independently selected from H, F, substituted or unsubstituted ($C_1$-$C_6$)alkyl and a substituted or unsubstituted ($C_1$-$C_6$)heteroalkyl group; $R_2$ is a moiety bearing a polar group if Y is other than $NR_3$ and is a moiety bearing a polar group, a substituted or unsubstituted ($C_1$-$C_{12}$)heteroalkyl group or a substituted or unsubstituted ($C_1$-$C_{12}$) alkyl group if Y is $NR_3$; each $R_3$ is independently selected from H, a substituted or unsubstituted ($C_1$-$C_{12}$)alkyl group, and a substituted or unsubstituted ($C_1$-$C_{12}$)heteroalkyl group, provided that neither of $R_2(R_1)_2C$ and $R_3$ contains a 2-chloroethyl or 2-hydroxyethyl group when Y equals $NR_3$; and each $R_4$ is independently selected from hydrogen, halogen, an amino group, a ($C_1$-$C_8$)alkylamino group, a di($C_1$-$C_8$)alkylamino group, a tri($C_1$-$C_8$)alkyl ammonium group, a hydroxyl group, a ($C_1$-$C_8$)alkoxy group, a thiol group, a ($C_1$-$C_8$)thioether group, a ($C_1$-$C_8$)sulfone group, a ($C_1$-$C_8$) sulfoxide group, a ($C_1$-$C_8$)sulfonamide group, a substituted or unsubstituted ($C_1$-$C_{12}$)alkyl group and a substituted or unsubstituted ($C_1$-$C_{12}$)heteroalkyl group.

Additionally, at least one of $R_2$, [Het], or [NABM] has a positive charge. In preferred embodiments, at least two of of $R_2$, [Het], or [NABM] has a positive charge. In still other preferred embodiments, at least one of $R_2$, [Het], or [NABM] carries two or more positive charges. Accordingly, in a particularly preferred embodiment, at least two among $R_2$, the heteroaromatic moiety [Het], and the NABM have a positive charge, so that compound (I) overall has at least two positive charges. Where it is stated that $R_2$, Het, or NABM has a positive charge, it does not mean that $R_2$ (or Het or NABM, as the case may be) is limited to having a single positive charge; multiple positive charges are also contemplated. Further, the state of being positively charged is in the context of approximately neutral aqueous or substantially aqueous conditions (e.g., a small amount of an organic solvent may be present), preferably under physiological conditions, i.e., a set of parameters that describe an intracellular (e.g., periplasm or cytoplasm) or extracellular environment. Such parameters include pH, temperature, ionic composition and strength, buffering capacity, etc., and these will vary depending upon various factors, including the host organism (e.g., animal or plant), the environment in which the compound is to be delivered, for example, into the blood of an animal or onto or into the soil in which a crop plant is, or is intended to, grow. A positive charge may result from the protonation of an amine, amidine, or guanidine group, or a less basic group such as a pyridine, pyridazine, pyrimidine, pyrazine, imidazole, or aniline group. Depending on such group's ionization constant, it may be substantially fully protonated or only partially protonated. Generally, as a matter of convenience, a group or moiety that may become positively charged by protonation is depicted in the structural formulae herein in its unprotonated form.

In other preferred embodiments, Y is $NR_3$ and $R_3$ is either H or lower alkyl. $R_1$ preferably is hydrogen. Exemplary suitable ($C_1$-$C_{12}$)alkyl or aryl groups for $R_2$, $R_3$, or $R_4$ include methyl, ethyl, propyl, isopropyl, n-butyl, s-butyl, isobutyl, cyclopentyl, cyclohexyl, phenyl, $C_6H_{11}CH_2$, $C_6H_5CH_2$, $C_5H_9CH_2$, and the like. In one group of preferred embodiments, the $C_1$-$C_{12}$ alkyl group is substituted with at least one substituent selected from ($C_1$-$C_4$)alkene group, a ($C_1$-$C_4$)alkyne group, an amino group, a ($C_1$-$C_8$)alkylamino group, a di($C_1$-$C_8$)alkylamino group, a tri($C_1$-$C_8$)alkyl ammonium group, a hydroxy group, a ($C_1$-$C_8$)alkoxy group, a thiol group, a ($C_1$-$C_8$)thioether group, a ($C_1$-$C_8$)sulfone group, a ($C_1$-$C_8$)sulfoxide group, a ($C_1$-$C_8$)sulfonamide group, a ($C_1$-$C_8$)acyl group, a mono or di($C_1$-$C_8$) N-alkylamide group, a thiol group, a ($C_1$-$C_4$)thioether group, a ($C_1$-$C_4$)sulfone group, a ($C_1$-$C_4$)sulfoxide group, a mono or di($C_1$-$C_8$) N-alkylsulfonamide group, a halogen, a ($C_3$-$C_7$) cycloaliphatic group, a five-, six- or seven-membered heterocyclic group, an aryl group, and a heteroaryl group. In some embodiments, the $(C_1-C_{12})$alkyl group is substituted with two, three or four of the functional group components provided above.

Returning to formula I, the polar group of $R_2$ can be a positively charged group such as a protonated primary, secondary, or tertiary amino group or a quaternary ammonium group. In some embodiments, the polar group will not be positively charged. Preferred examples of uncharged polar groups include hydroxy, cyano, fluoro, ether, ketone, sulfonamido, sulfone, and carboxamido groups, although other suitable polar groups may be employed. Here, a polar region is one that has a dipole moment greater than that of a C—C or C—H covalent bond.

For those preferred embodiments in which Y is $NR_3$, the $R_2$ group need not contain a polar group. In such instances, $R_2$ may be equal to $R_3$—that is the partial formula $R_2(CR_1)_2$ Y reduces to $R_3(CR_1)_2NR_3$, where the two $R_3$'s are independently variable. The two $R_3$'s may be joined to form a ring structure, preferably containing 4, 5, 6, or 7 atoms. The ring may contain heteroatom moieties, such as —NH—, —NMe—, —O—, —N(lower alkyl)-, —S—, —SO$_2$—, —SO—, and the like as part of the ring. The ring also may contain substituents pendant therefrom. Suitable substituents are provided in the definitions of alkyl and aryl substituents, above.

For those embodiments in which NABM is positively charged, the positive charge may be situated in a moiety pendant from the side of NABM (i.e., from an internal heteroaromatic or aliphatic moiety) and/or in a terminal moiety distal from Het. The positively charged moiety may be derived from a basic amino acid (e.g., lysine, histidine, or arginine) or a peptide unit comprising one or more basic amino acids. A preferred peptide configuration is one in which a proline separates two basic amino acids (e.g., Arg-Pro-Arg). Exemplary suitable positively charged moieties are disclosed in Dervan et al., WO 98/37087 (1998) and Rothbard et al., WO 98/52614 (1998), the disclosures of which are incorporated herein by reference. As those in the art will appreciate, however, the NABM need not always have a positive charge, as illustrated by compound X (infra).

As described above, the nucleic acid binding moiety [NABM] may be a dsDNA intercalator, a dsDNA minor groove binding moiety, or a dsDNA major groove binding moiety. It is to be understood that, where [NABM] is referred to as a "minor groove binder" (or words to that effect), it does not mean that such moiety has binding interactions exclusively with the minor groove; the moiety also may have binding interactions with other parts of the dsDNA, for example, with adjacent base pairs by intercalation, with backbone phosphate groups, or with the major groove.

[NABM] preferably is a minor groove binder, which typically (but not necessarily) has an elongate crescent shape, topologically complementary to the shape of the minor groove. The minor groove binder may be a residue of a naturally occurring compound, such as doxorubicin, daunomycin, anthramycin, calicheamycin, mitomycin, CC-1065, duocarmycin, distamycin, and netropsin, or an analog or a derivative thereof. Alternatively, [NABM] may be a residue of a synthetic minor groove binder, such as pentamidine, berenil, stilbamidine, DDUG, NSC 101327, SN 6999, SN 6136, SN 16814, SN18071, NSC 57153, Hoechst 33258, Ionen X, and methyl green, or an analog or a derivative thereof.

In particularly preferred embodiments, the nucleic acid binding moiety is a synthetic polyamide unit comprising N-methylpyrrole carboxamide ("Py") units and optionally one or more of N-methylimidazole carboxamide ("Im"), N-methyl-3-hydroxypyrrole carboxamide ("Hp"), glycine carboxamide, β-alanine carboxamide, γ-aminobutyric acid carboxamide, 5-aminovaleric acid carboxamide, and γ-2,4-diaminobutyric acid carboxamide units, such units being represented respectively by the structures:

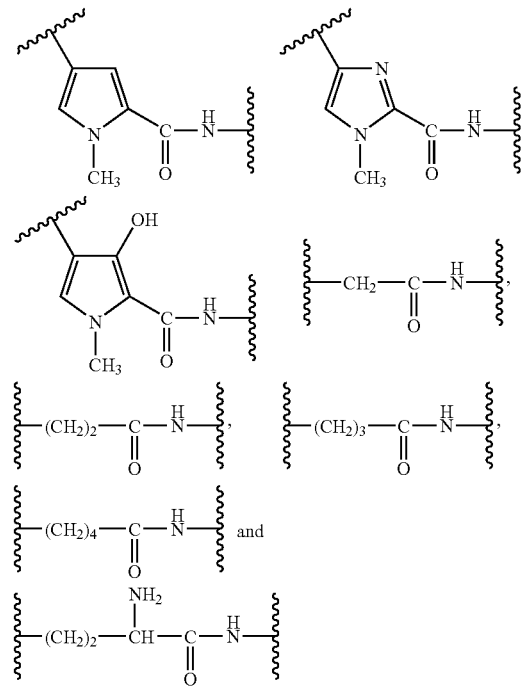

Some polyamides similar to those described herein have been shown to be minor groove binders, often binding with high binding constants (e.g., greater than $10^9$ M$^{-1}$). Disclosures relating to the design and synthesis of such polyamides include Baird and Dervan, *J. Am. Chem. Soc.* 118, 6141-6146 (1996) and U.S. applications Ser. No. 08/607,078 (filed Feb. 26, 1996); Ser. No. 09/374,702 (filed Aug. 12, 1999); Ser. No. 09/372,473 (filed Aug. 11, 1999); Ser. No. 09/372,474 (filed Aug. 11, 1999); Ser. No. 09/414,611 (filed Oct. 8, 1999); and Ser. No. 09/479,279 (filed Jan. 5, 2000 and entitled "Compositions and Methods Relating to Cyclic Compounds that Undergo Nucleotide Base Pair Specific Interactions with Double Stranded Nucleic Acids"), the disclosures of which are incorporated herein by reference. It has been further discovered that such polyamides can bind to dsDNA with two heteroaromatic carboxamide moieties fitting side-by-side within the minor groove and that such side-by-side heteroaromatic carboxamide pairs recognize specific dsDNA base pairs, giving rise to a set of "pairing rules" correlating heteroaromatic carboxamide pairs and the DNA base pairs recognized:

| Heteroaromatic Pair | dsDNA Base Pair(s) Recognized |
|---|---|
| Im/Py | G/C |
| Py/Im | C/G |
| Py/Py | A/T, T/A |
| Hp/Py | T/A |
| Py/Hp | A/T |

Accordingly, the pairing rules above can be used to design an NABM moiety that binds to dsDNA with specificity for particular base pair sequences.

Glycyl or β-alanyl carboxamides can serve as "spacer" groups for adjusting the position of the heteroaromatic carboxamide residues in relation to the nucleotide base pairs of the NABM's binding site. A γ-aminobutyric acid carboxamide, 5-aminovaleric acid carboxamide, or γ-2,4-diaminobutyric acid carboxamide unit (or other moieties that produce a substantially equivalent structural effect) introduces a "hairpin" into the polyamide and permits heteroaromatic carboxamide units of the same NABM to bind side-by-side to each other. Use of two such units, for example, at each end of the NABM or at one end and at an internal position, allows the formation of NABMs having other conformations (e.g., cyclic or "H-pin" conformations, respectively). The 2-amino group of γ-2,4-diaminobutyric acid provides an attachment point for tandem-linked polyamide units, as well as providing a moiety that can be used to introduce chirality into the NABM. A Py, Hp, or Py equivalent heteroaromatic carboxamide may be replaced with a β carboxamide to form pairs such as β/β or β/Py. These and other molecular design principles disclosed in the aforementioned references may be used in the design of preferred examples NABM moieties of this invention.

In yet other embodiments, nucleic acid binding moiety [NABM] comprises the structure (II)

$$\text{-}Q_1\text{-}Z_1\text{-}Q_2\text{-}Z_2\text{-}\ldots\text{-}Q_m\text{-}Z_m\text{-} \quad (II)$$

where each of $Q_1, Q_2, \ldots, Q_m$ is a heteroaromatic moiety or $(CH_2)_p$ and the subscript p is an integer from 1 to 3, inclusive; each of $Z_1, Z_2, \ldots, Z_m$ is a covalent bond or a linking group; and the subscript m is an integer from 1 to 9, inclusive, more preferably from 2 to 4. For those embodiments in which Q is a heteroaromatic moiety, it is preferably selected from optionally substituted imidazole, pyrrole, pyrazole, furan, isothiazole, oxazole, isoxazole, thiazole, thiophene, furazan, 1,2,3-thiadiazole, 1,2,4-thiadiazole, 1,2,5-thiadiazole, 1,3,4-thiadiazole, 1,2,3-triazole, 1,2,4-triazole, 1,3,4-oxadiazole, 1,2,4-oxadiazole, and thiophene moieties. Exemplary substituents include Cl, F, $CH_3$ (e.g., as in N-methylpyrrole or N-methylimidazole), and hydroxy (e.g., as in 3-hydroxypyrrole).

Linking groups $Z_1, Z_2, \ldots Z_m$, are generally those divalent groups having from 2 to 5 backbone atoms. The term "backbone" as applied to linking groups in the present invention, refers to the atoms that are in a contiguous linkage between the two groups the atoms are joining. For example, two heteroaromatic moieties that are connected by —C(O)NH— are said to be linked by a group having two "backbone" atoms (e.g., the carbon atom and the nitrogen atom). Exemplary linking groups include carboxamide, amidine, and ester groups, as respectively illustrated below, with carboxamide groups being preferred:

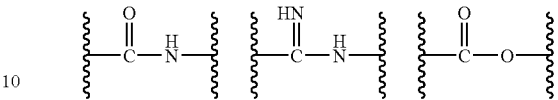

In still other embodiments of the invention, the nucleic acid binding moiety comprises the structure (III)

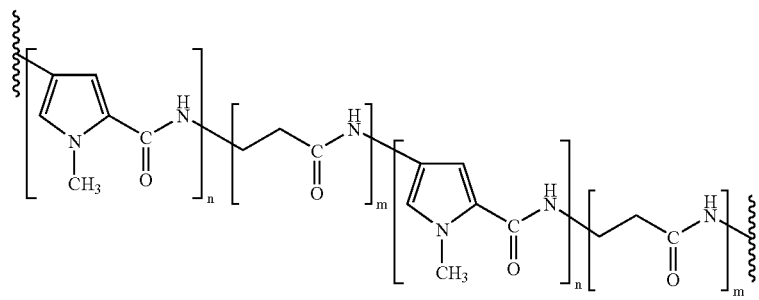

where each n is independently an integer from 1 to 9, inclusive (preferably n is 2 or 3), and each m is independently 0 or 1 (preferably 1).

As noted above, the heteroaromatic moiety [Het] and NABM are joined by a linking group L, which can be a covalent bond or a divalent linking group having from 2 to 5 (preferably 2) backbone atoms. Exemplary linking groups include carboxamide, amidine, and ester groups, with carboxamide linking groups being preferred. Exemplary substituents for the [Het] groups include Cl, F, $CH_3$ (e.g., as in N-methylpyrrole or N-methylimidazole), and hydroxy (e.g., as in 3-hydroxypyrrole).

A variety of synthetic methods may be used to link Het and NABM. In addition to those described in the examples further below, other methods known in the art may be used. Several such methods are cited here for illustrative purposes, with a distamycin residue as the NABM. An amine-terminated distamycin residue may be alkylated with an epoxide compound, as taught in Arcamone et al., U.S. Pat. No. 4,738,980 (1988) and U.S. Pat. No. 4,766,142 (1988). Another approach is provided in Lazzari et al., U.S. Pat. No. 5,017,599 (1991); U.S. Pat. No. 5,049,579 (1991); and U.S. Pat. No. 5,310,752 (1994) and Animati et al., U.S. Pat. No. 5,670,534 (1997): condensation of an acyl compound with an amino-terminated distamycin residue in the presence of a condensing agent such as dicyclohexylcarbodiimide to form a carboxamide linkage. Animati et al., U.S. Pat. No. 5,412,976 (1995) discloses the reaction of a carboxyimidate with an amine-terminated distamycin residue to form an amidine. The aforementioned patents are incorporated herein by reference.

The heteroaromatic moiety may be a substituted or unsubstituted form of any of the following: imidazole, pyrrole other than N-methyl or N-hydrogen pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,2,4-oxadiazole, 1,3,4-oxadiazole, or thiophene moiety.

Preferably, Het is an isothiazole, as in

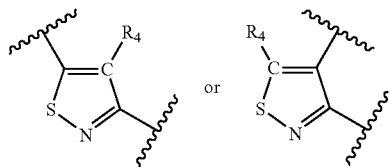

Preferred isothiazole-containing compounds according to this invention are represented by formula (IVa):

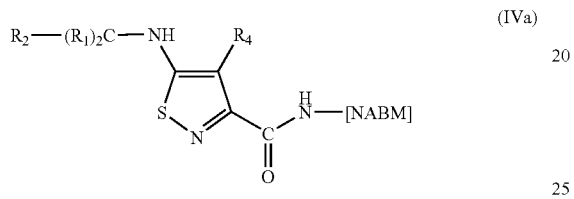

(IVa)

In compound (IVa), $R_1$, $R_2$, and $R_4$ are as previously defined, with reference to formula I.

Particularly preferred isothiazole-containing compounds of this invention comprise the structure (IVb)

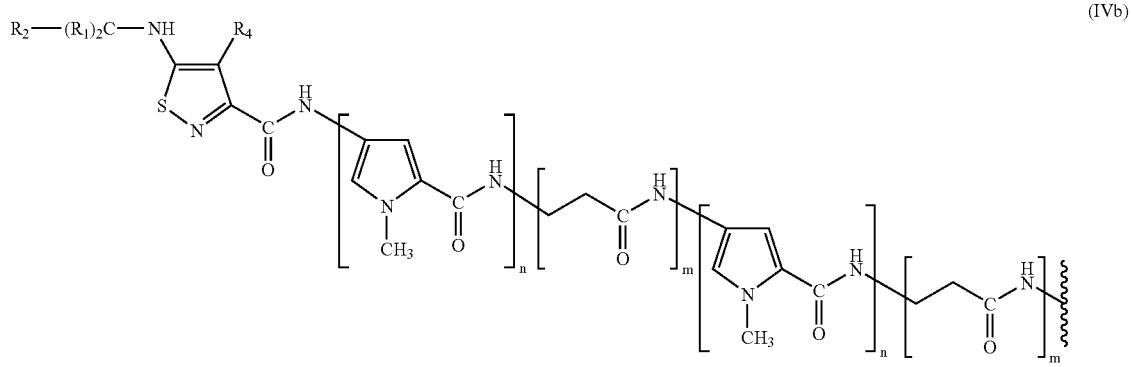

(IVb)

where m, n, $R_1$, $R_2$, and $R_4$ are as previously defined.

In $R_2(R_1)_2C$—Y—, (shown more specifically in IVb as $R_2(R_1)_2C$—NH) the polar group(s) in $R_2$ (where present) are preferably one or more primary, secondary, or tertiary amino groups, which when protonated, make $R_2$ positively charged. Alternatively, the polar group is a quaternary ammonium group. In other preferred groups, each $R_1$ is hydrogen. More preferably, $R_2$ has an amino group separated from the Y group by about 2 to about 6 atoms. An exemplary but not exhaustive listing of specific moieties within these preferences is given below (with the group Y also shown to indicate the attachment position):

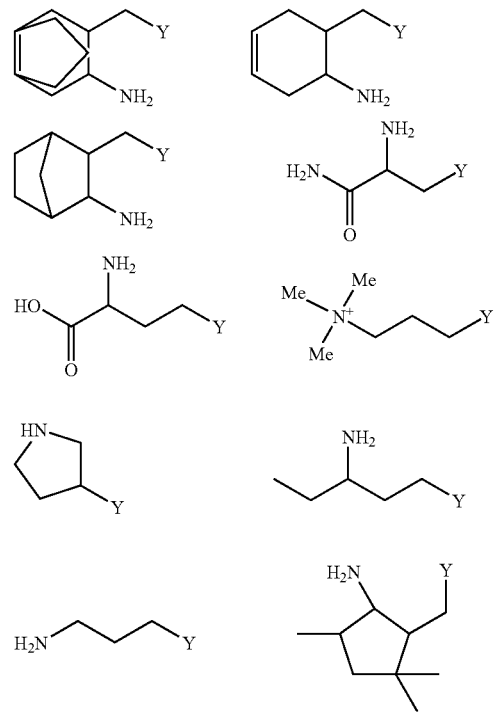

-continued

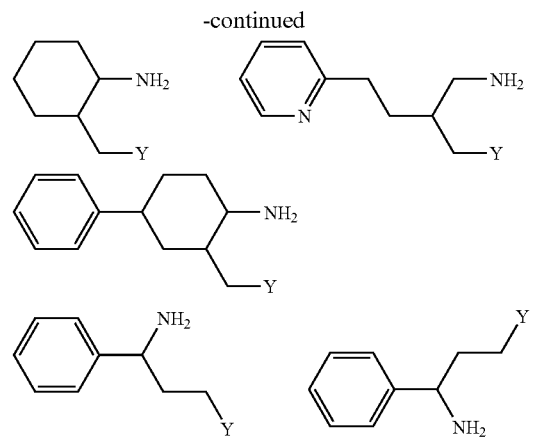

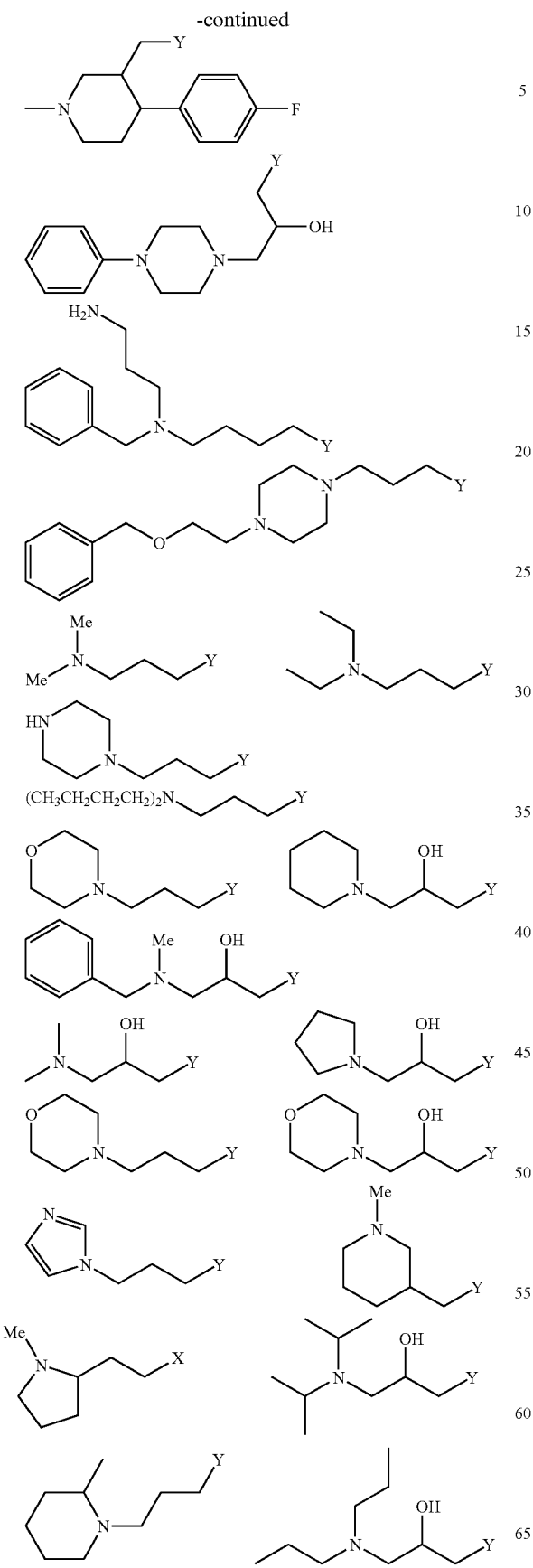
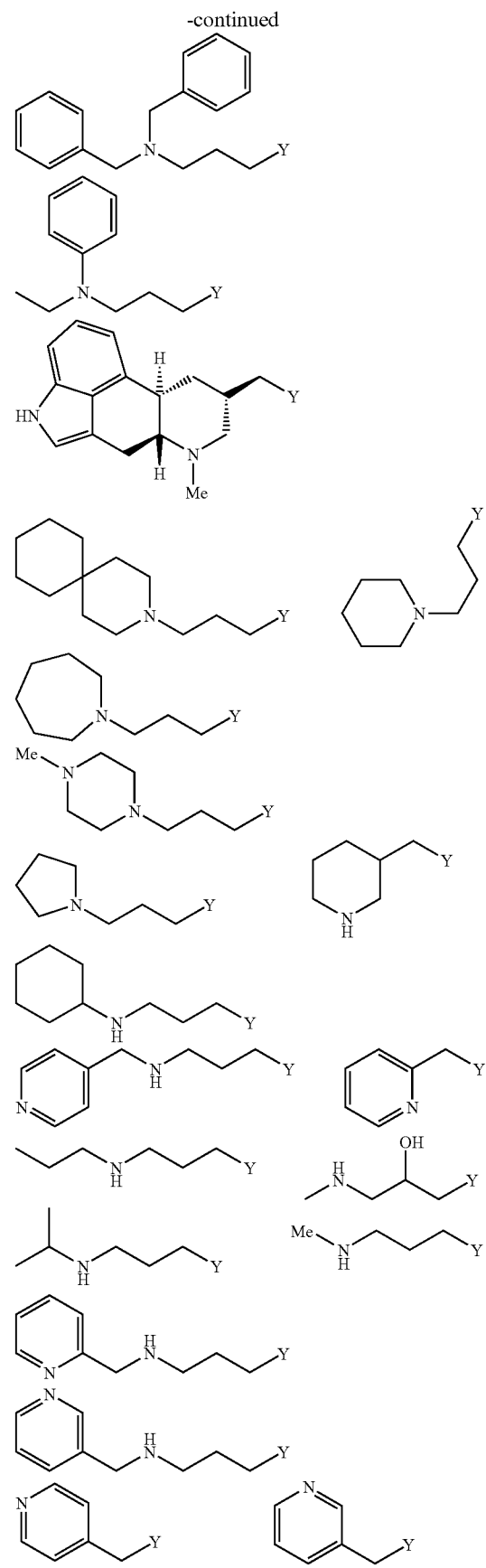

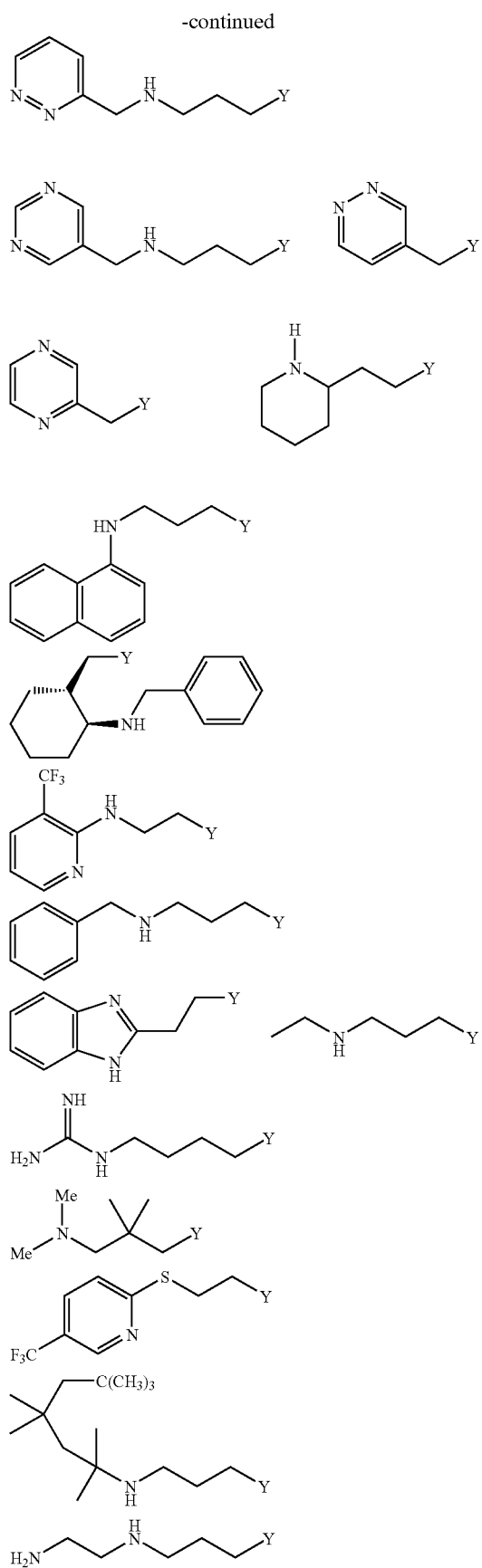

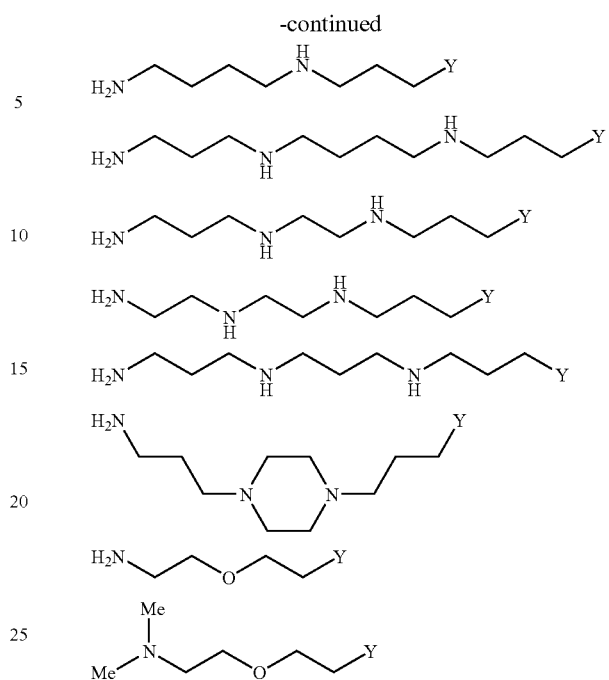

In the preceding compounds, where an amino group is separated from Y by one or more methylene (CH$_2$) groups, higher or lower homologs may be used, provided the separation between Y and the amino group is kept between about 2 and 6 atoms.

In other embodiments, Y is NR$_3$ in which R$_3$ is an alkyl or heteroalkyl group, or is optionally linked to R$_2$ to form a cyclic structure. The ring thus formed can contain additional heteroatom moieties, such as —NH—, —NMe—, —O—, —N(lower alkyl)-, and the like as part thereof and may be substituted or unsubstituted, as illustrated below:

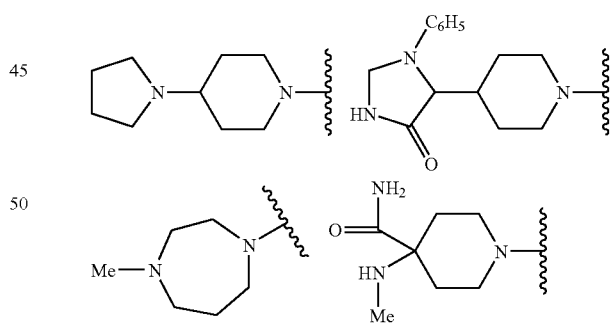

Generally, R$_2$ will bear a polar group. For those embodiments in which Y is NR$_3$, the presence of one polar group (Y) will reduce the need for additional polar groups on R$_2$. In such instances, R$_2$ may be equal to R$_3$—that is the partial formula R$_2$(CR$_1$)$_2$Y reduces to R$_3$(CR$_1$)$_2$NR$_3$, where the two R$_3$'s are independently variable.

Turning now to a series of particularly preferred compounds represented by the formula (Ia), repeated below for convenience, specific and/or preferred embodiments relating thereto are now discussed in detail.

(Ia)

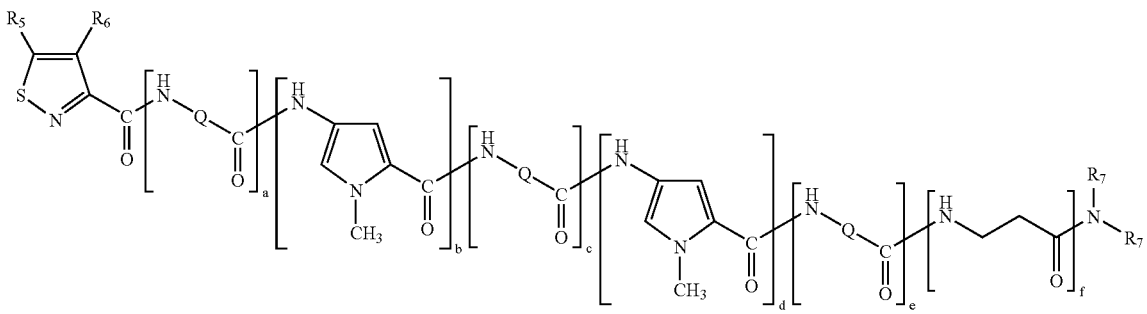

In formula Ia, Each Q is independently selected from —(CH$_2$)$_2$—, —(CH$_2$)$_3$—, and a heteroaromatic ring independently selected from substituted or unsubstituted imidazole, pyrrole, pyrazole, furan, isothiazole, oxazole, isoxazole, thiazole, furazan, 1,2,3-thiadiazole, 1,2,4-thiadiazole, 1,2,5-thiadiazole, 1,3,4-thiadiazole, 1,2,3-triazole, 1,2,4-triazole, 1,2,4-oxadiazole, 1,3,4-oxadiazole, and thiophene rings. Preferably, Q is a thiophene ring. Exemplary substituents include Cl, F, CH$_3$ (e.g., as in N-methylpyrrole or N-methylimidazole), and hydroxy (e.g., as in 3-hydroxypyrrole).

The subscripts a, b, and d are each independently 0, 1, 2, 3, 4, or 5, with the proviso that at least one of a, b, or d is other than 0. The subscripts c, e and f are each independently 0 or 1.

In the preferred embodiments of formula Ia, R$_5$ is selected from halogen, OR$_7$ and N(R$_7$)$_2$. More preferably, R$_5$ is selected from halogen and N(R$_7$)$_2$. R$_6$ is selected from hydrogen, halogen, a substituted or unsubstituted (C$_1$-C$_{12}$) alkyl group and a substituted or unsubstituted (C$_1$-C$_{12}$) heteroalkyl group. When either of R$_5$ or R$_6$ is halogen, chlorine and fluorine are preferred, with chlorine being the most preferred. Each R$_7$ is independently selected from hydrogen, a substituted or unsubstituted (C$_1$-C$_{12}$)alkyl group and a substituted or unsubstituted (C$_1$-C$_{12}$)heteroalkyl group. The alkyl groups in R$_6$ and R$_7$ can be, for example, methyl, ethyl, propyl, isopropyl, butyl, s-butyl, isobutyl, t-butyl, pentyl, cyclopentyl, benzyl, or cyclohexyl, with methyl being preferred. In some embodiments, the (C$_1$-C$_{12}$) alkyl and heteroalkyl groups are substituted with functional groups such as alkene; alkyne; hydroxy; primary, secondary, or tertiary amine; quaternary ammonium; alkoxy; acyl; amide; thiol; thioether; sulfoxide; sulfonamide; halogen; a cycloaliphatic group; a heterocyclic group; an aromatic group; a heteroaromatic group; and the like; and combinations thereof.

In N(R$_7$)$_2$, one preferred embodiment is each R$_7$ is hydrogen. In another preferred embodiment, one R$_7$ is hydrogen and the other R$_7$ is methyl.

Where R$_5$ is N(R$_7$)$_2$, the two R$_7$'s optionally can be joined to form a substituted or unsubstituted 4, 5, 6, or 7 membered ring optionally containing an —NH—, —NMe—, —O—, or N-lower alkyl group as part of the ring. Exemplary embodiments of these compounds are shown by the partial formulae below:

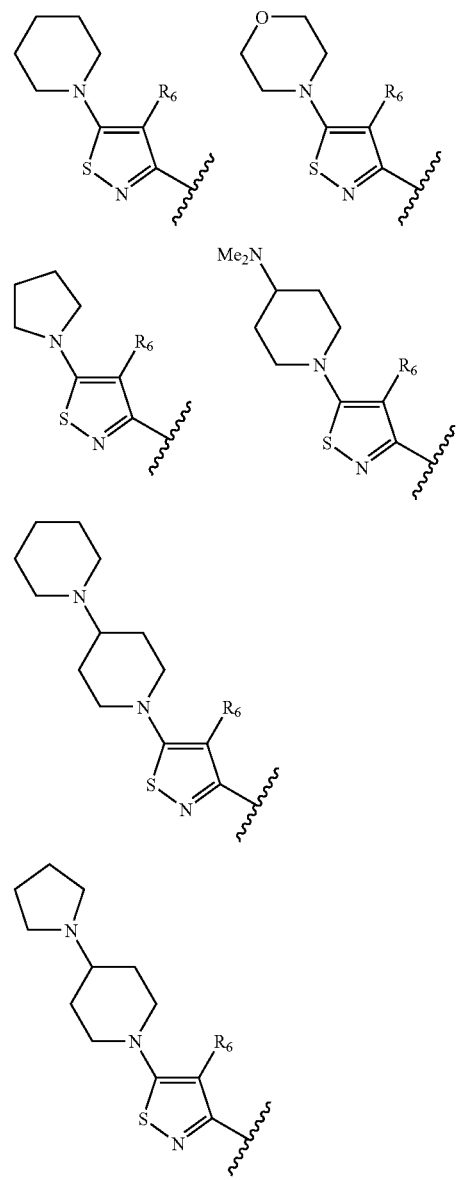

-continued

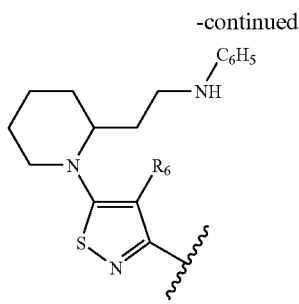

The 4, 5, 6, or 7 member ring formed by N(R$_7$)$_2$ may substituted or unsubstituted. In particular, the substituent may be or may contain an amino group.

Specific preferred combinations of R$_2$, R$_1$, and Y to form the partial structure

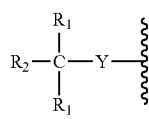

in formula (I), above, and specific R$_5$'s in formula (Ia), above, are given below:

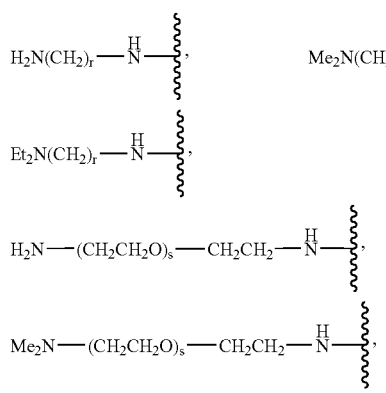

-continued

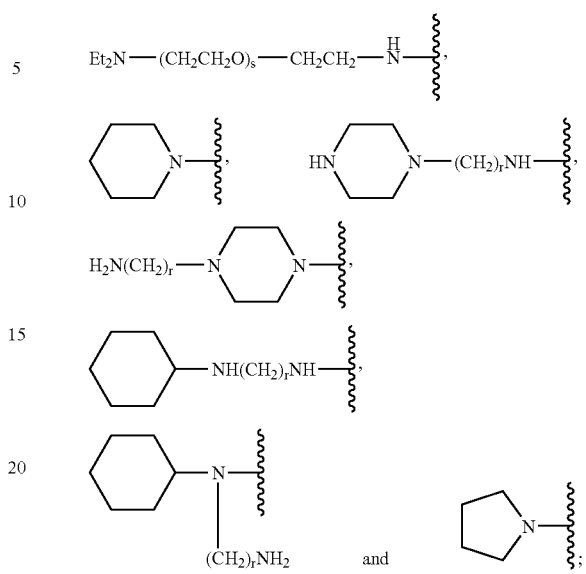

wherein r is 2, 3, or 4 and s is 1, 2, 3, 4, 5, or 6.

In view of the foregoing, below are disclosed preferred compounds within the scope of this invention:

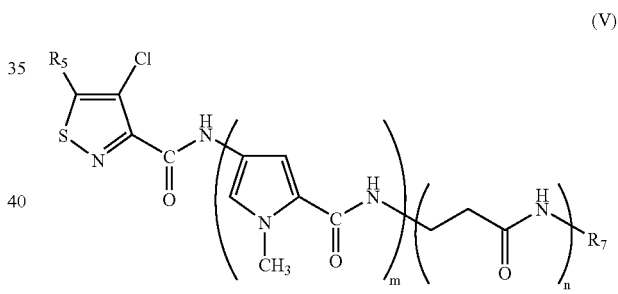

(V)

In formula V, R$_5$ and R$_7$ have the meanings previously provided for formula Ia; m is 2, 3, or 4 and n is 0 or 1. At least one of R$_5$ and R$_7$ is a positively charged group.

| Compound | m | n | R$_5$— | —R$_7$ |
|---|---|---|---|---|
| V-a | 3 | 0 | H$_2$N~~~NH~ | ~N(Me)(CH$_2$)$_3$—N(Me)Me |
| V-b | 3 | 0 | H$_2$N~~NH~ | ~N(Me)(CH$_2$)$_3$—N(Me)Me |

-continued

| Compound | m | n | R₅— | —R₇ |
|---|---|---|---|---|
| V-c | 3 | 0 | H₂N–CH₂CH₂–NH– | –(CH₂)₄–N(Me)₂ |
| V-d | 3 | 0 | Cl– | –(CH₂)₄–N(Me)₂ |
| V-e | 3 | 0 | H₂N–(CH₂)₄–NH– | –(CH₂)₄–N(Me)₂ |
| V-f | 3 | 0 | CF₃(CF₂)₂–CH₂CH₂–NH– | –(CH₂)₄–N(Me)₂ |
| V-g | 3 | 0 | H₂N–(CH₂)₃–NH– | –(CH₂)₃–NH–C₆H₁₁ |
| V-h | 3 | 0 | C₆H₁₁–NH–(CH₂)₃–NH– | –(CH₂)₃–NH–C₆H₁₁ |
| V-i | 3 | 0 | C₆H₁₁–NH–(CH₂)₃–NH– | –H |
| V-j | 3 | 0 | C₆H₁₁–NH–(CH₂)₃–NH– | –(CH₂)₂–morpholinyl |
| V-k | 3 | 0 | C₆H₁₁–NH–(CH₂)₃–NH– | –(CH₂)₄–NH₂ |
| V-l | 3 | 0 | Cl– | –(CH₂)₃–NH–C₆H₁₁ |
| V-m | 3 | 0 | morpholinyl–(CH₂)₂–NH– | –(CH₂)₂–C(=NH)NH₂ |

-continued
| Compound | m | n | R₅— | —R₇ |
|---|---|---|---|---|
| V-n | 3 | 0 |  |  |
| V-o | 3 | 0 | 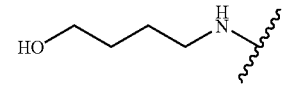 | 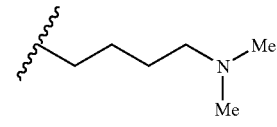 |
| V-p | 3 | 0 | 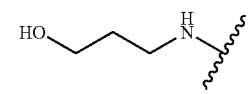 | 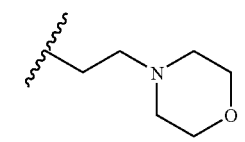 |
| V-q | 3 | 0 | 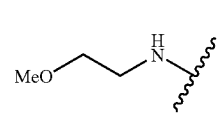 | 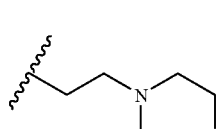 |
| V-r | 2 | 1 | 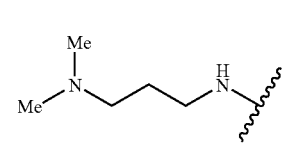 | 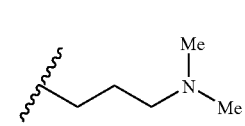 |
| V-s | 2 | 1 | 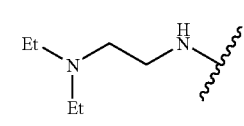 | 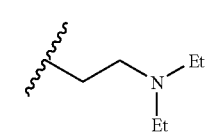 |
| V-t | 4 | 1 | 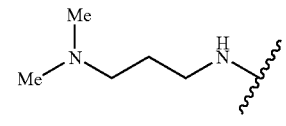 | 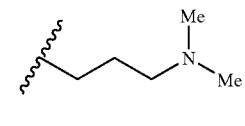 |
| V-u | 3 | 1 |  | 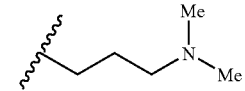 |
| V-v | 3 | 0 |  | 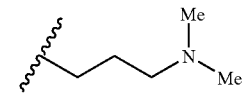 |
| V-w | 3 | 0 |  | 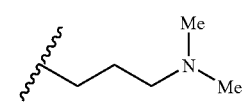 |

-continued
| Compound | m | n | R₅— | R₇— |
|---|---|---|---|---|
| V-x | 3 | 0 | ,  (mixture) | 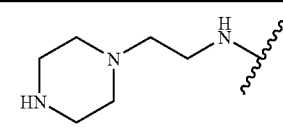 |
| V-aa | 3 | 0 | 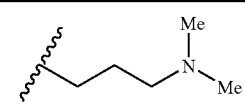, 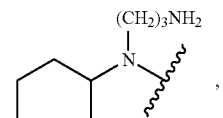 (mixture) | 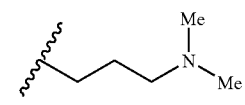 |
| V-bb | 2 | 0 | 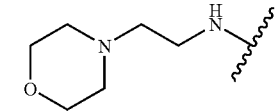 | 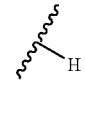 |
| V-cc | 2 | 1 | 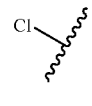 | 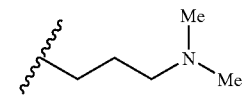 |
| V-dd | 3 | 0 | 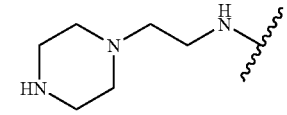, 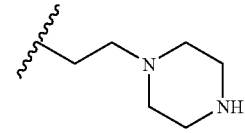 (mixture) |  |
| V-ee | 3 | 0 | 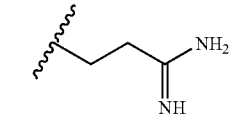 | 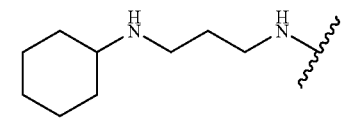 |
| V-ff | 3 | 0 | 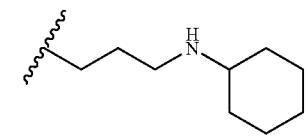 |  |

-continued

| Compound | m | n | R₅— | —R₇ |
|---|---|---|---|---|
| V-gg | 3 | 0 | morpholine-CH₂CH₂-NH- | -CH₂CH₂CH₂-morpholine |
| V-hh | 3 | 0 | piperidine-N- | -CH₂CH₂CH₂-morpholine |
| V-ii | 3 | 0 | piperazine(HN)-CH₂CH₂-NH- | -(CH₂)₄-NH₂ |
| V-jj | 3 | 0 | MeO- | -CH₂CH₂CH₂-C(=NH)NH₂ |
| V-kk | 3 | 0 | H₂N-CH₂CH₂CH₂-NH- | -(CH₂)₄-N(Me)Me |
| V-ll | 3 | 0 | piperazine(HN)-CH₂CH₂-NH- , H₂N-CH₂CH₂-piperazine-N- (mixture) | -(CH₂)₄-N(Me)Me |
| V-mm | 3 | 0 | Cl- | -CH₂CH₂CH₂-morpholine |
| V-nn | 3 | 0 | Cl- | -CH₂CH₂CH₂-C(=NMe)NHMe |
| V-oo | 3 | 0 | MeO- | -CH₂CH₂CH₂-NH-C(=NH)NH₂ |

-continued
| Compound | m | n | R₅— | —R₇ |
|---|---|---|---|---|
| V-pp | 3 | 0 | Cl— | —CH₂CH₂C(=NNHMe)NH₂ |
| V-qq | 3 | 0 | H₂N-CH₂CH₂-NH— | —(CH₂)₂-(4,5-dihydroimidazol-2-yl) |
| V-rr | 3 | 0 | MeO-(CH₂)₃-NH— | —(CH₂)₃-morpholin-4-yl |
| V-ss | 3 | 0 | EtO-(CH₂)₃-NH— | —(CH₂)₃-morpholin-4-yl |
| V-tt | 3 | 0 | cyclopropyl-CH₂-NH— | —(CH₂)₃-morpholin-4-yl |
| V-uu | 3 | 0 | Cl— | —(CH₂)₂-(4,5-dihydroimidazol-2-yl) |
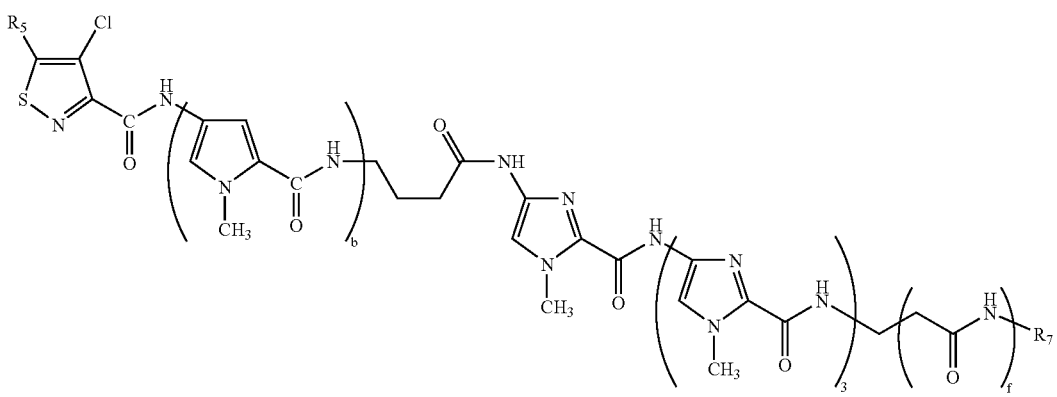
(VI)

In formula VI, b is 1, 2, 3, or 4, f is 0 or 1, and $R_5$ and $R_7$ are as previously defined. At least one of $R_5$ and $R_7$ contains a positively charged group.
| Compound | b | f | $R_5$— | —$R_7$ |
|---|---|---|---|---|
| VI-a | 3 | 1 | Cl— | —(CH₂)₄N(Me)₂ |
| VI-b | 3 | 1 | Me₂N(CH₂)₃NH— | —(CH₂)₄N(Me)₂ |
| VI-c | 2 | 1 | Cl— | —(CH₂)₄N(Me)₂ |
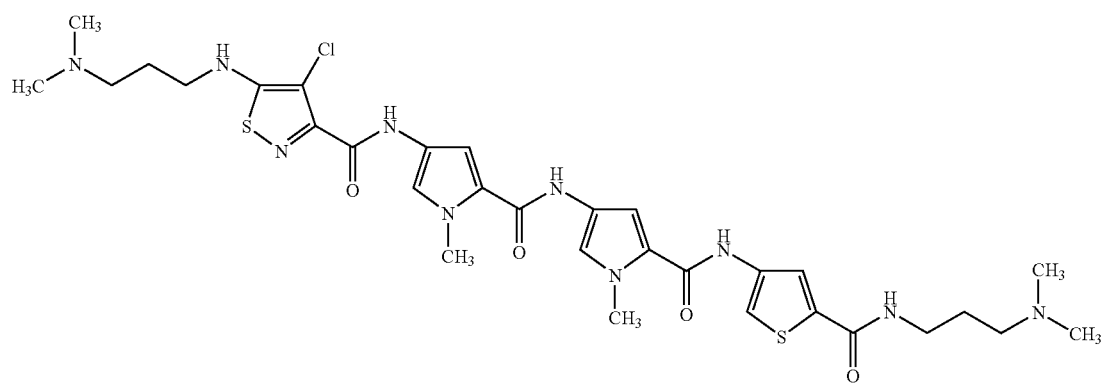
(VII)
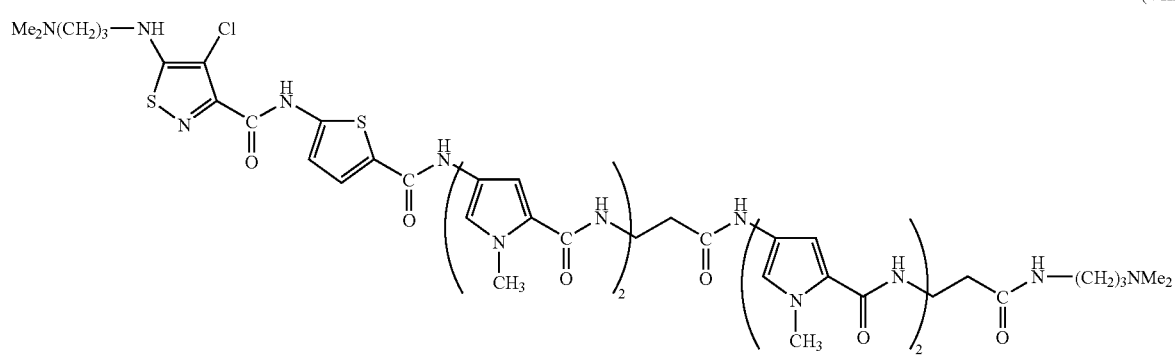
(VIII)
(IX)

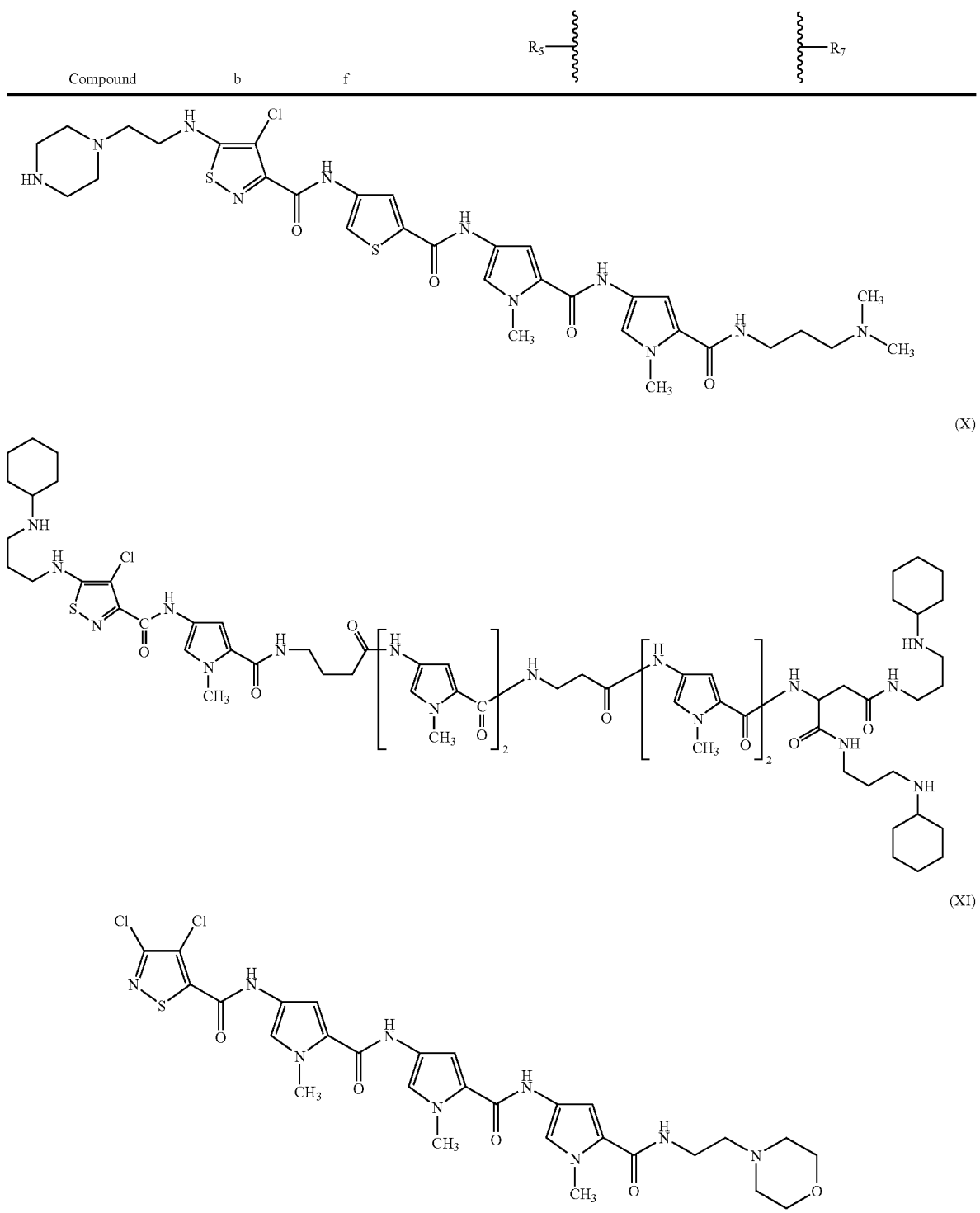

The structures of foregoing compounds were confirmed by at least one of $^1$H-NMR and mass spectrometry. In most instances, both $^1$H-NMR and mass spectra were obtained.

Pharmaceutically acceptable salts of compounds of this invention include salts of their conjugate acids or bases. Exemplary suitable counterions for conjugate acid salts include the chlorides, bromides, phosphates, sulfates, maleates, malonates, salicylates, fiunarates, ascorbates, methanesulfonates, malates, citrates, acetates, tartrates, succinates, glutamates, and the like, in particular those salts which are FDA acceptable. A conjugate acid salt may be formed by contacting a compound in the free base form with a sufficient amount of the desired acid. A conjugate acid or base form of a compound of this invention is considered equivalent to the free base form (or the free acid form, as the case may be) for the purposes of the claims of this invention.

Compounds of this invention are useful because they are strong DNA binders, often as nanobinders (i.e., association constant ($K_a$) of $10^9$ $M^{-1}$) or even as picobinders ($K_a$ of $10^{12}$ $M^{-1}$). It is especially noteworthy that some compounds of the invention are nanobinders while having relatively few heteroaromatic moieties (3-5), while previously described nanobinders have generally required a larger number of heteroaromatic moieties.

Additionally, compounds of this invention have been found to have anti-fungal (e.g., yeast, filamentous fungi) and/or anti-bacterial (gram-positive, gram-negative, aerobic, anaerobic) properties and therefore may be used for combating (i.e., preventing and/or treating) infections by such pathogens. Other pathogens against which compounds of this invention may be used include protozoa and viruses. For human anti-infective applications, a compound of this invention may be used in combination with a pharmaceutically acceptable carrier. The composition may be dry, or it may be a solution. Treatment may be reactive, for combating an existing infection, or prophylactic, for preventing infection in an organism susceptible to infection.

Host organisms that may be treated include eukaryotic organisms, in particular plants and animals. The plant may be an agriculturally important crop, such as wheat, rice, corn, soybean, sorghum, and alfalfa. Animals of interest include maninals such as bovines, canine, equines, felines, ovines, porcines, and primates (including humans).

While not wishing to be bound by any particular theory, it is believed that the compounds of this invention derive their biological activity by binding to double stranded nucleic acid, in particular double stranded DNA.

The matching of a compound of this invention against a particular pathogen may be accomplished by rational design if the desired target dsDNA base pair sequence—e.g., a sequence in a gene (or a regulatory region thereof, e.g., a promoter, enhancer) that is critical to proliferation of the pathogen—is known. In such circumstances, a nucleic acid binding moiety that binds to the target base pair sequence with the desired degree of specificity is preferably used. The NABM may be a residue of a naturally occurring dsDNA binder with known specificity for the target sequence, or may be a synthetic dsDNA binder synthesized according to the base pair recognition rules discussed hereinabove. Alternatively, the matching may be accomplished by a screening method, comprising the steps of (a) providing a compound of this invention to a population of pathogenic organisms and (b) determining whether the compound inhibits proliferation of the population of pathogenic organisms. A specific target pathogen may be screened against a library of compounds to determine which one(s) are effective against it. Conversely, a specific compound may be screened against a number of pathogens, to determine which one(s) it is effective against.

The practice of this invention may be further understood by reference to the following examples, which are provided by way of illustration and not of limitation.

Synthesis

A solid-phase and a solution-phase method are each described with reference to particular compounds. However, those skilled in the art will understand these methods are general in nature and that other compounds of this invention can be synthesized by variations in the provided descriptions, with the appropriate substitution of starting materials, intermediates, and/or reagents.

Exemplary Solid-phase Synthesis

The solid phase synthesis of compound V-s is described in this section, as exemplary.

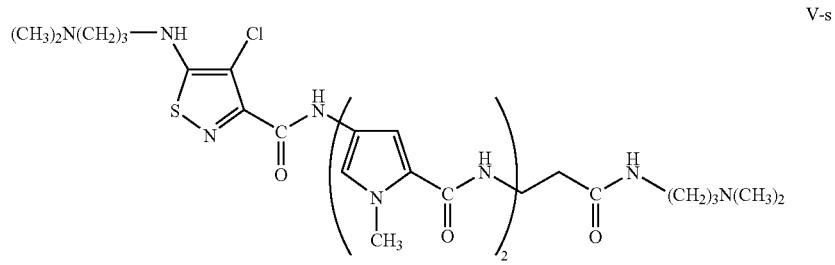

V-s

The starting point is commercially available Boc-β-alanine-PAM-resin (see also Dervan et al., U.S. Pat. No. 6,090,947 (2000)). This resin has a Boc-protected β-alanyl residue attached to polystyrene resin via a phenylacetamidomethyl (PAM) linkage:

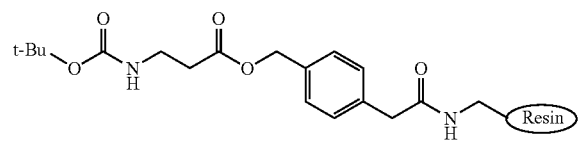

Boc-β-alanine-PAM resin

Several "shorthand" notations will be used hereinafter, to make the formulas more compact. "β" denotes the β-alanyl residue

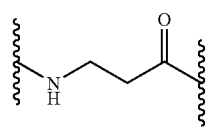

"PAM" denotes
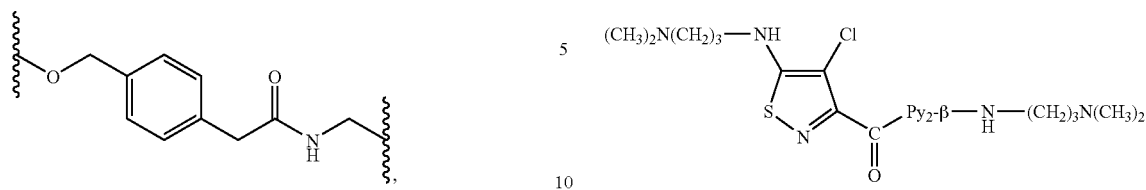
Boc refers to the butyloxycarbonyl protective group (t-BuOC=O). "Py" denotes the residue
represents compound V-s, and Boc-Py$_2$-OH represents
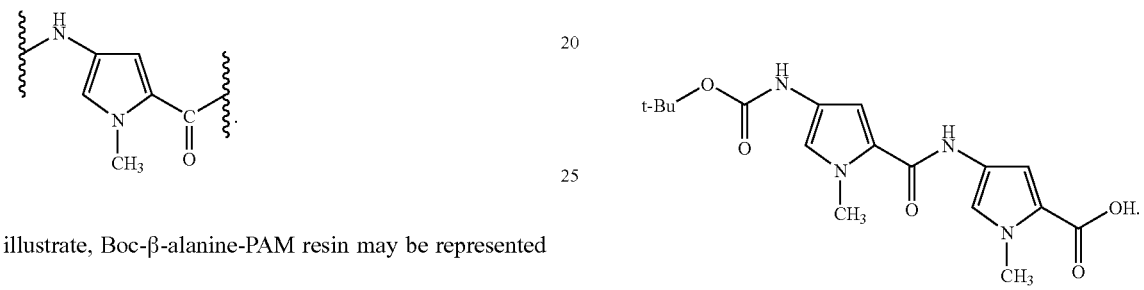
To illustrate, Boc-β-alanine-PAM resin may be represented as
Boc-β-PAM-(Resin),
the formula
Scheme A below summarizes the synthetic route to compound V-s (shown in the scheme as A-4):
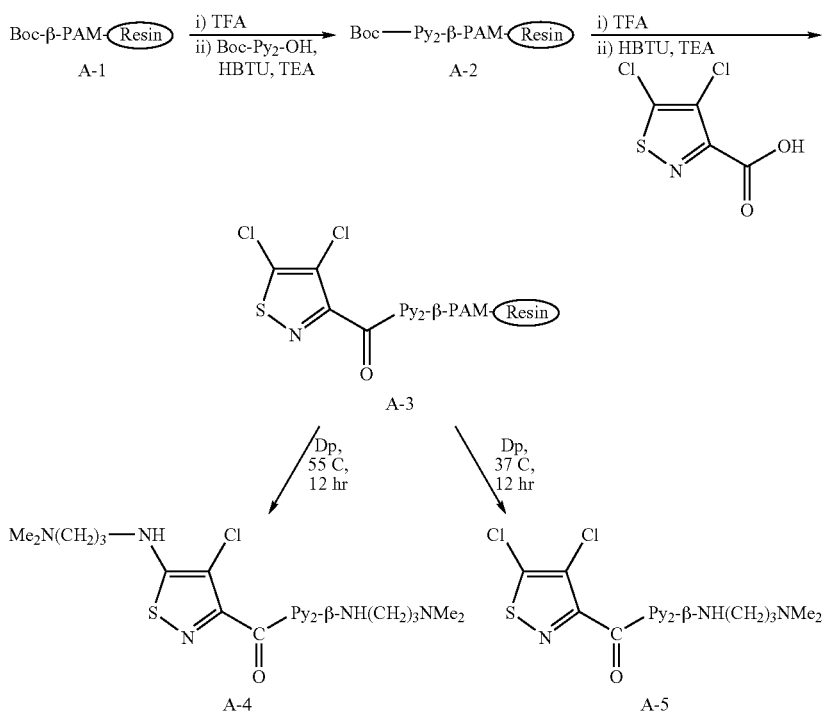

Coupling of Boc-Py$_2$OH to Boc-β-PAM resin. 1.25 grams Boc-β-alanine-PAM resin (0.88 mmole/gram, A-1 in Scheme A) was treated with 30 mL trifluoroacetic acid (TFA) for 1 hour. The resin was air dried after washing with chloroform, methanol, and diethyl ether.

0.48 grams BocPy$_2$OH (1.3 mmole, 1.2 eq) was activated with 0.49 grams of 2-(1H-benzotriazole-1-yl)-1,1,3,3-tetramethyluronium hexafluorophosphate ("HBTU," 1.3 mmole, 1.2 eq) in 2 mL DMF and 1 mL triethylamine (TEA) for 10 min at 37° C. The resulting solution was added to the dried resin, followed by enough DMF to make a slurry, and put at 37° C. for 3 hours with shaking. 1 mL of acetic anhydride was added and the resin treated at room temperature for 30 min, to yield Boc-Py$_2$-β-PAM resin (A-2 in Scheme A).

Deprotection of Boc-Py$_2$-β-PAM resin and coupling to 4,5-dichloroisothiazole-3-carboxylic acid. The resin was filtered, washed with DMF, washed with chloroform, then treated with 100 mL TFA for 1 hour and then dried as before, to yield the deprotected H-Py$_2$-β-PAM resin.

4,5-Dichloroisothiazole-3-carboxylic acid (0.26 grams, 1.3 mmole, 1.2 eq) was activated with 0.48 grams HBTU (1.3 mmole, 1.2 eq) in 2 mL DMF and 1 mL triethylamine (TEA) for 5 min at room temperature. The resulting solution was added to the dried resin, followed by enough DMF to make a slurry, and put at 37° C. for 3 hours with shaking to yield the resin-coupled isothiazole intermediate shown as A-3 in Scheme A.

Reaction with 3-(dimethylamino)propylamine—decoupling from resin with simultaneous substitution in isothiazole ring. To produce compound V-s and decouple it from the solid-phase support, the intermediate A-3 was treated with 3 mL 3-(dimethylamino)propylamine ("Dp") at 55° C. for 12 hours. The solution was then filtered, washed with glacial acetic acid, diluted to 14 mL with glacial acetic acid, and purified by preparative HPLC to yield compound V-s (shown as A-4 in Scheme A)

Reaction with 3-(dimethylamino)propylamine—decoupling from resin without substitution in isothiazole ring. Treatment with Dp under milder conditions results in decoupling only, substantially without substitution at one of the chlorines in the isothiazole group. Thus, treatment with 1.5 mL DMF and 1.5 mL Dp at 37° C. for 12 hours, followed by filtration, washing with glacial acetic acid, dilution to 14 mL with glacial acetic acid, and purification by preparative HPLC yielded the dichloro compound V-cc (shown as A-5 in Scheme A).

Preparative HPLC was performed under the following conditions: Hamilton PRP-1 reversed phase column, 250 mm×21.5 mm; solvent A: 0.5% acetic acid; solvent B: acetonitrile; 0-60% B in 180 min.

Pure fractions were lyophilized to provide 5-30 mg product.

Compound V-cc (and its analogs) is not only a useful precursor for the synthesis of other compounds according to this invention by substitution of one of the isothiazole chlorines, but in its own right was a good binder for dsDNA and had significant anti-pathogenic properties.

Exemplary Solution-phase Synthesis

This example describes illustratively the solution synthesis of compounds such as V-a, V-b, and V-c. First, Scheme B below describes the synthesis of intermediate compound B-8 (or H-Py$_3$-OH per the above described shorthand notation).

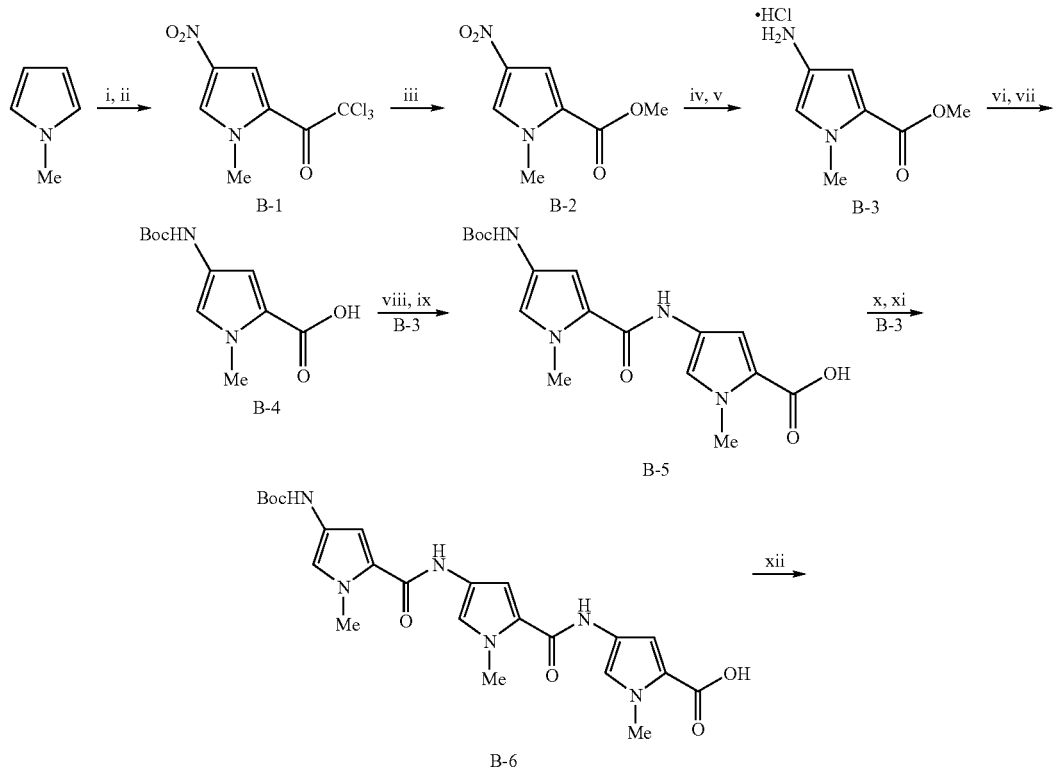

Scheme B

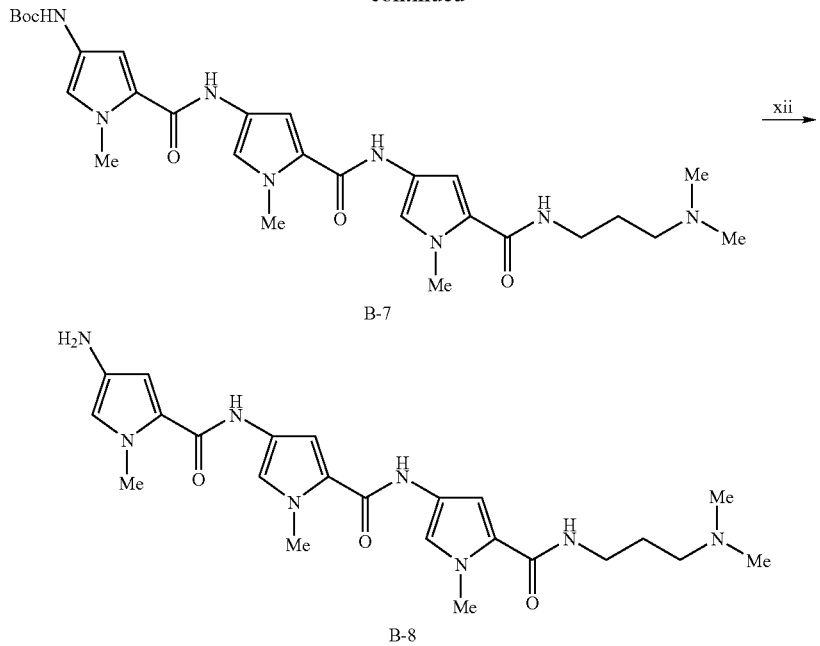

(i) trichloroacetyl chloride, Et₂O  (ii) 90% nitric acid, Ac₂O
(iii) NaOMe/MeOH  (iv) H₂ (1 atm), 10% Pd/C, EtOAc
(v) HCl, Et₂O  (vi) 10% K₂CO₃ (aq), Boc-anhydride
(vii) NaOH, MeOH, H₂O, 60 C  (viii) DCC, HOBt, DMF, TEA
(ix) NaOH, MeOH, H₂O 60 C  (x) HBTU, DMF, TEA
(xi) NaOH, MeOH, H₂O, 60 C  (xii) H₂N(CH₂)₃NMe₂
(xiii) trifluoroacetic acid 4-nitro-2-trichloroacetyl-1-methylpyrrole (B-1). To a well stirred solution of trichloroacetyl chloride (1 kg, 5.5 mole) in 1.5 liter ethyl ether in a 12 liter flask was added dropwise over a period of 3 h a solution of N-methylpyrrole (0.45 kg, 5.5 mole) in 1.5 liter anhydrous ethyl ether. The reaction was stirred for an additional 3 hours and quenched by the dropwise addition of a solution of 400 g potassium carbonate in 1.5 liters water. The layers were separated and the ether layer concentrated in vacuo to provide 2-(trichloroacetyl)pyrrole (1.2 kg, 5.1 mol) as a yellow crystalline solid sufficiently pure to be used without further purification. To a cooled (−40° C.) solution of 2-(trichloroacetyl) pyrrole (1.2 kg, 5.1 mol) in acetic anhydride (6 L) in a 12 L flask equipped with a mechanical stirrer was added 440 mL fuming nitric acid over a period of 1 hour while maintaining a temperature of (−40° C.). The reaction was carefully allowed to warm to room temperature and stir an additional 4 h. The mixture was cooled to −30° C., and isopropyl alcohol (6 L) added. The solution was stirred at −20° C. for 30 min during which time a white precipitate forms. The solution was allowed to stand for 15 min and the resulting precipitate collected by vacuum filtration to provide 4-nitro-2-trichloroacetyl-1-methylpyrrole, shown as compound B-1 in Scheme B (0.8 kg, 54% yield) TLC (7:2 benzene/ethyl acetate) Rf 0.7; $^1$H NMR (DMSO-$d_6$) δ 8.55 (d, 1H, J=1.7 Hz), 7.77 (d, 1H, J=1.7 Hz), 3.98 (s, 3H); $^{13}$C NMR (DMSO-$d_6$) δ 173.3, 134.7, 133.2, 121.1, 116.9, 95.0, 51.5; IR (KBr) 1694, 1516, 1423, 1314, 1183, 1113, 998, 750. FABMS m/e 269.936 (M+H 269.937 calc. for $C_7H_5N_2O_3Cl_3$).

Methyl 4-nitropyrrole-2-carboxylate (B-2). To a solution of compound B-1 (800 g, 2.9 mol) in 2.5 L methanol in a 4 L Erlenmeyer flask equipped with a mechanical stirrer was added dropwise a solution of NaH (60% dispersion in oil) (10 g, 0.25 mol) in 500 mL methanol. The reaction was stirred 2 h. at room temperature, and quenched by the addition of conc. sulfuric acid (25 mL). The reaction was then heated to reflux, allowed to slowly cool to room temperature as Methyl 4-nitropyrrole-2-carboxylate (shown as compound B-2 in Scheme B) crystallizes as white needles which were collected by vacuum filtration and dried in vacuo. (450 g, 47% yield). TLC (ethyl acetate) Rf 0.8; $^1$H NMR (DMSO-$d_6$) δ 8.22 (d, 1H, J=1.7 Hz), 7.22 (d, 1H, J=1.6 Hz), 3.88 (s, 3H), 3.75 (s, 3H); $^{13}$C NMR (DMSO-$d_6$) δ 37.8, 52.2, 112.0, 123.0, 129.9, 134.6, 160.3; IR (KBr) 3148, 1718, 1541, 1425, 1317, 1226, 1195, 1116, 753. FABMS m/e 184.048 (M+H 184.048 calc. for $C_7H_8N_2O_4$).

Methyl 4-amino-1-methyl-pyrrole-2-carboxylate hydrochloride (B-3). Compound B-2 (450 g, 2.8 mol) was dissolved in ethyl acetate (8 L). A slurry of 40 g of 10% Pd/C in 800 mL ethyl acetate was then added and the mixture stirred under a slight positive pressure of hydrogen (c.a. 1.1 atm) for 48 h. Pd/C was removed by filtration through Celite, washed 1×50 mL ethyl acetate, and the volume of the mixture reduced to c.a. 500 mL. 7 L of cold ethyl ether was added and HCl gas gently bubbled through the mixture. The precipitated amine hydrochloride was then collected by vacuum filtration to yield (380 g, 81.6%) of methyl 4-amino-1-methyl-pyrrole-2-carboxylate hydrochloride (shown as compound B-3 in Scheme B) as a white powder. TLC (ethyl acetate) Rf(amine) 0.6, Rf salt (0.0), $^1$H NMR (DMSO-$d_6$) δ 10.23 (br s, 3H), 7.24 (d, 1H J=1.9), 6.79 (d, 1H, J=2.0), 3.83 (s, 3H), 3.72 (s, 3H) $^{13}$C NMR (DMSO-$d_6$) δ 160.8, 124.3, 121.2, 113.4, 112.0, 51.8, 37.1; IR (KBr) 3095, 2693, 1709, 1548, 1448, 1266, 1102, 802, 751. FABMS m/e 154.075 (154.074 calc. for $C_7H_{10}N_2O_2$). 4-[(tert-butoxycarbonyl)amino]-1-methylpyrrole-2-carboxylic acid (B-4). Compound B-3 (340 g, 1.8 mol) was dissolved in 1 L of 10% aqueous sodium carbonate in a 3 L flask equipped with a mechanical stirrer, di-t-butyldicarbonate (400 g, 2.0 mmol) slurried in 500 mL of dioxane was added over a period of thirty min maintaining a temperature of 20° C. The reaction was allowed to proceed for three h and was determined complete by TLC, cooled to 5° C. for 2 h and the resulting white precipitate collected by vacuum filtration. The Boc-pyrrole ester contaminated with Boc-anhydride was dissolved in 700 mL MeOH, 700 mL of 2M NaOH was added and the solution heated at 60° C. for 6 h. The reaction was cooled to room temperature, washed with ethyl ether (4×1000 mL), the pH of the aqueous layer reduced to c.a. 3 with 10% (v/v) $H_2SO_4$, and extracted with ethyl acetate (4×2000 mL). The combined ethyl acetate extracts were dried (sodium sulfate) and concentrated in vacuo to provide a tan foam. The foam was dissolved in 500 mL of DCM and 2 L petroleum ether added, the resulting slurry was concentrated in vacuo. The reaction was redissolved and concentrated three additional times to provide (320 g, 78% yield) of 4-[(tert-butoxycarbonyl)amino]-1-methylpyrrole-2-carboxylic acid (shown as compound B-4 in Scheme B) as a fine white powder. TLC (7:2 benzene/ethyl acetate v/v) Rf (ester) 0.8, Rf (acid) 0.1. (ethyl acetate), Rf (acid) 0.6, $^1H$ NMR (DMSO-$d_6$) δ 12.10 (s, 1H), 9.05 (s, 1H), 7.02 (s, 1H), 6.55 (s, 1H), 3.75 (s, 3H), 1.41 (s, 9H) $^{13}C$ NMR (DMSO-$d_6$) δ 162.4, 153.2, 123.3, 120.1, 119.2, 107.9, 78.9, 36.6, 28.7.; IR(KBr) 3350, 2978, 1700, 1670, 1586, 1458, 1368, 1247, 1112, 887, 779. FABMSm/e 241.119(M+H241.119 calc. for $C_{11}H_{17}N_2O_4$).

4-[(tert-butoxycarbonyl)amino]-1-methylpyrrole-2-(4-carboxamido-1-methylpyrrole)-2-carboxylic acid (B-5). To a solution of compound B4 (40 g, 167 mmol) in 150 mL DMF was added 1.2 eq HOBt (27 g, 0.2 mmol) followed by 1.2 eq DCC (40.4 g, 0.2 mmol). The solution was stirred for 5 h, and the DCU removed by filtration, and rinsed with 50 mL of DMF. Compound B-3 (34 g, 160 mmol) was added, followed by TEA (80 mL) and the reaction stirred at 50° C. for 10 h. The reaction mixture was then added dropwise to a stirred solution of ice water (2 L) and the solution placed at 4° C. overnight. The resulting precipitate was collected by vacuum filtration and dried overnight to provide ethyl 4-[(tert-butoxycarbonyl)amino]-1-methylpyrrole-2-(4-carboxamido-1-methyl imidazole)-2-carboxylate (53 g, 83% yield). The ester was dissolved in 200 mL methanol and 3M NaOH (200 mL) added and the resulting mixture stirred for 3 h at 50° C. Excess methanol was removed in vacuo and the resulting solution acidified by the addition of 2 M HCl. The resulting precipitate of 4-[(tert-butoxycarbonyl)amino]-1-methylpyrrole-2-(4-carboxamido-1-methylpyrrole)-2-carboxylic acid (shown as compound B-5 in Scheme B) was collected by vacuum filtration and dried in vacuo to yield a white powder. (43 g, 90% yield).

4-[(tert-butoxycarbonyl)amino]-1-methylpyrrole-2-(4-carboxamido-1-methylpyrrole)-2-(4-carboxamido-1-methylpyrrole)-2-carboxylic acid (B-6). 150 mL of DMF, followed by 80 mL of TEA was added to a mixture of compound B-5 acid (50 g, 139 mmol) and 0.98 eq HBTU (51 g). The solution was stirred for 2 h at rt. 1.1 eq of compound B-3 (28.9 g) was added, and the reaction stirred at 50° C. for 30 h. The reaction mixture was then added dropwise to a stirred solution of ice water (1.2 L) and the solution the resulting precipitate was collected by vacuum filtration and dried overnight to provide the methyl ester of compound B-6 (59 g, 85% yield). The ester was dissolved in 200 mL methanol and 2.5M NaOH (200 mL) added and the resulting mixture stirred for 10 h at 50° C. Excess methanol was removed in vacuo and the resulting solution acidified by the addition of 2 M H2SO4. The resulting precipitate of 4-[(tert-butoxycarbonyl)amino]-1-methylpyrrole-2-(4-carboxamido-1-methylpyrrole)-2-(4-carboxamido-1-methylpyrrole)-2-carboxylic (shown as compound B-6 in Scheme B) was collected by vacuum filtration and dried in vacuo to yield a white powder. (51 g, 87% yield).

Reaction of Compound B-6 with 3-(dimethylamino)propylamine. Compound B-6 was converted to the corresponding amide with 3-(dimethylamino)propylamine (compound B-7 in Scheme B) by the following procedure: Compound B-6 (46.8 grams, 0.1 mmole, 1 eq) was activated with HBTU (34.4 grams, 0.095 mmole, 0.95 eq) in 50 mL DMF and 25 mL TEA for 45 min at room temperature. 3-(Dimethylamino)propylamine (12 mL, 0.12 mmole, 1.2 eq) was added and the reaction was stirred at 37° C. overnight. The product mixture containing compound B-7 was concentrated in vacuo.

Deprotection of Compound B-7. To approximately 30 grams compound B-7 was added 150 mL trifluoroacetic acid. The reaction was stirred overnight at room temperature. The product compound B-8 was concentrated in vacuo and approximately 40 mL acetic acid and 200 mL water was added (enough acetic acid to prevent precipitation) and the solution was extracted with diethyl ether three times. Compound B-8 was purified by preparative HPLC (Hamilton PRP-1 reversed phase column, 250 mm×101.6 mm; solvent A: 0.5% acetic acid, solvent B: acetonitrile; 0-100% B in 180 min).

Coupling of Compound B-8 with 4.5-dichloroisothiazole-3-carboxylic acid. 2 grams 4,5-dichloroisothiazole-3-carboxylic acid (10 mmole, 1.2 eq) was activated with 3.7 grams HBTU (9.8 mmole, 1.14 eq) in 20 mL DMF and 10 mL triethylamine. The solution was stirred for 10 minutes at room temperature. Compound B-8 (4 grams, 8.5 mmole, 1 eq) was added as a solid, and 4 mL DMF added to complete the transfer. The resulting solution was stirred at 37° C. overnight. The reaction was then dried in vacuo, 200 mL 10% aqueous acetic acid was added and the product was purified by preparative HPLC. (Hamilton PRP-1 reversed phase column, 250 mm×101.6 mm; solvent A: 0.5% acetic acid; solvent B: acetonitrile; 0-60% B in 320 min). Pure fractions were lyophilized to provide 2 grams product compound V-v (3.1 mmole, 36% yield). Compound V-v can be used for the synthesis of a variety of compounds by substitution of the C-5 chlorine with an appropriate amine, alkoxide, or thiolate. In the case of reaction with a thiolate, the resulting thioether may be oxidized to the corresponding sulfone or sulfoxide. Further, the compound may have alkylating activity.

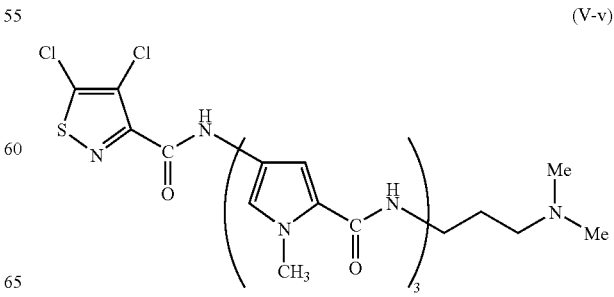

(V-v)

Aminolysis of Compound V-v. The following procedure generally describes the aminolysis of Compound V-v to yield compounds such as V-a, V-b, or V-c. 20 mg of Compound XII was dissolved in 1 mL of neat amine (or 1 gram of amine with 1 mL DMF if the amine is a solid at room temperature). The amines are 4-(dimethylamino)butylamine, 3-(dimethylamino)propylamine, and 2-(dimethylamino)ethylamine for the syntheses of compounds V-a, V-b, and V-c, respectively. The reaction was heated at 55° C. for 15 hours, then cool to room temperature. Acetic acid was added to a total volume of 14 mL and the product mixture was loaded onto a preparative HPLC column (Hamilton PRP-1 reversed phase column, 250 mm×21.5 mm). Solvent A: 0.5% aqueous acetic acid; solvent B: acetonitrile; 0-60% solvent B in 180 min.

The compound structures of this invention were confirmed by mass spectroscopy or $^1$H-NMR spectroscopy, or in most instances, both. The spectra were in each instance consistent with the assigned structures.

Binding to dsDNA

Quantitative DNase I footprint titration experiments of polyamide NABMs indicate that the isothiazole group has a preference for binding opposite G relative to T, A, and C. While not excluding other mechanisms, it is likely that the N2 nitrogen of the isothiazole ring makes a specific hydrogen bond with the N2 exocyclic amine group of G. The DNA-binding affinities of the isothiazole containing polyamides reveal that this interaction is likely energetically favored relative to the comparable interaction of the N-methylimidazole-2-carboxamide group with G. Surprisingly, the affinities of a number of polyamides containing the isothiazole heterocycle and not more than a total of four heterocycle rings are greater than about $10^9$ M$^{-1}$. Polyamides containing the isothiazole group can bind to DNA via a variety of binding motifs including but not limited to side-by-side overlapped "2:1" polyamide-DNA-binding, side-by-side slipped 2:1 polyamide-DNA-binding, hairpin polyamide-DNA-binding, and 1:1 polyamide-DNA-binding. For 2:1 polyamide-DNA binding, the isothiazole group is preferably paired with a 5-aminopyrrole-2-carboxylic acid residue or its analogs or 0-alanine residue or its analogs. Binding studies further indicate that polyamides containing the isothiazole group can bind DNA with both a 5'-3' N-terminus-to-C-terminus (N—C), DNA-strand—polyamide orientation as well as a 5'-3∝ C—N DNA strand—polyamide orientation. Molecules that present a positively charged moiety on both the C-terminal and N-terminal ends most likely bind the 5'-3' C—N orientation preferentially.

A partial nucleotide sequence of a dsDNA restriction fragment used for footprinting experiments is:

(SEQ ID NO:1)
5'-CTAGATGCCGCTAAGTACTATGCCGCTAACTACTATGCCGCTAATTA
CT ATGCCGCTAAATACTATGCCGCTAACTAGTATGCCGCTATGCA-3'.

Other DNA molecules having a nucleotide sequence to be tergeted by a NABM can be readily synthesized according to well known methods.

The binding data for representative compounds appears below in Table A

TABLE A dsDNA Binding Results

Sequence, Binding Constant (M$^{-1}$)

| Compound | AGTACT | ACTACT | ATTACT | AATACT | TGGTCA |
|---|---|---|---|---|---|
| V-u | 1 × 10$^{11}$ | 1 × 10$^9$ | 5 × 10$^8$ | 1 × 10$^8$ | — |
| V-t | 2 × 10$^8$ | 2 × 10$^8$ | 2 × 10$^8$ | 2 × 10$^8$ | 1 × 10$^{10}$ |
| V-c | 5 × 10$^9$ | 2 × 10$^8$ | 2 × 10$^8$ | 2 × 10$^8$ | — |
| V-b | 3 × 10$^9$ | 2 × 10$^8$ | 1 × 10$^8$ | 1 × 10$^8$ | — |
| V-a | 3 × 10$^9$ | 1 × 10$^8$ | 1 × 10$^8$ | 1 × 10$^8$ | — |
| VI-a | 2 × 10$^{10}$ | 2 × 10$^9$ | 2 × 10$^9$ | 2 × 10$^9$ | — |
| VI-b | 1 × 10$^{11}$ | 7 × 10$^9$ | 7 × 10$^9$ | 7 × 10$^9$ | — |
| VI-c | 2 × 10$^8$ | 1 × 10$^8$ | 1 × 10$^{10}$ | 1 × 10$^9$ | — |
| XII (comparative) | 3 × 10$^9$ | 5 × 10$^8$ | 5 × 10$^8$ | 5 × 10$^8$ | — |

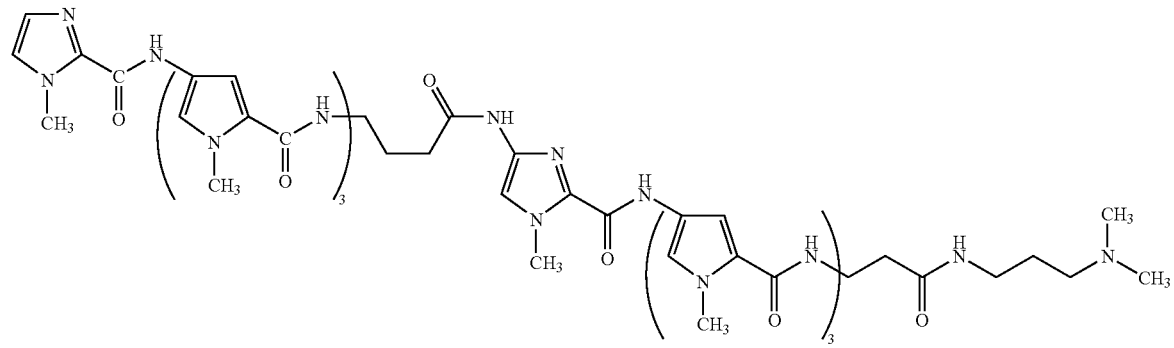

(XII)

Compounds V-u, V-c, V-b, and V-a were screened on a restriction fragment containing over 300 different 6-bp sites. Each of these compounds was found to bind preferentially to an AGTACT site with subnanomolar affinities ranging from 1×10$^{11}$ M$^{-1}$ to 3×10$^9$ M$^{-1}$. It is notable that these affinities are significantly higher than expected for compounds containing 4 heterocycles. Specificity against the single base pair mismatch sites ACTACT, ATTACT, and AATACT was determined to range from 200-fold to 11-fold for each of these compounds. Compound V-t was found to bind a TGGTCA site with an affinity of $1 \times 10^{10}$ $M^{-1}$ preferentially to AGTACT, ACTACT, ATTACT, or AATACT. The mechanism of this binding is not certain, but may involve either a "slipped" 2:1 binding mode (see, e.g., U.S. Pat. No. 6,090,947) or a 1:1 binding mode. Compounds VI-a and VI-b most likely adopt hairpin conformations. Each of these compounds was found to bind preferentially to an AGTACT site with subnanomolar affinities of $2 \times 10^{10}$ $M^{-1}$ and $1 \times 10^{11}$ $M^{-1}$ respectively. Each of these DNA-binding affinities is 9-30 fold higher than that of the comparison compound XII, having an isothiazole ring replaced by an imidazole ring. Compound VI-c was observed to bind ATTACT, and AATACT preferentially to ACTACT and AGTACT, potentially as a single base mismatch. The optimal target sequence for this compound may be WGWCWW (W=A or T).

Exemplary protocol for DNaseI footprint titration experiments. All reactions were executed in a total volume of 400 μL. A polyamnide stock solution or $H_2O$ (for reference lanes) was added to an assay buffer containing 3'-$^{32}$p radiolabeled restriction fragment (20,000 cpm), affording final solution conditions of 10 mM Tris.HCl, 10 mM KCl, 10 mM $MgCl_2$, 5 mM $CaCl_2$, pH 7.0. The solutions were allowed to equilibrate for at least 12 hours at 22° C. Footprinting reactions were initiated by the addition of 10 μL of a stock solution of DNase I (at the appropriate concentration to give ~55% intact DNA) containing 1 mM dithiothreitol and allowed to, proceed for 7 minutes at 22° C. The reactions were stopped by the addition of 50 μL of a solution containing 2.25 M NaCl, 150 mM EDTA, 23 μM base pair calf thymus DNA, and 0.6 mg/ml glycogen, and ethanol precipitated. The reactions were resuspended in 1×TBE/80% formamide loading buffer, denatured by heating at 85° C. for 15 minutes, and placed on ice. The reaction products were separated by electrophoresis on an 8% polyacrylamide gel (5% crosslinking, 7 M urea) in 1×TBE at 2000 V for 1.5 h. Gels were dried on a slab dryer and then exposed to a storage phosphor screen at 22° C.

Quantitative DNase I Footprint Titration Data Analysis. Background-corrected volume integration of rectangles encompassing the footprint sites and a reference site at which DNase I reactivity was invariant across the titration generated values for the site intensities ($I_{site}$) and the reference intensity ($I_{ref}$). The apparent fractional occupancy ($\theta_{app}$) of the sites were calculated using the equation:

$$\theta_{app} = 1 - \frac{I_{site}/I_{ref}}{I^\circ_{site}/I^\circ_{ref}} \quad (1)$$

where $I_{site}^\circ$ and $I_{ref}^\circ$ are the site and reference intensities, respectively, from a DNase I control lane to which no polyamide was added.

The ($[L]_{tot}$, $\theta_{app}$) data were fit to a Langmuir binding isotherm (eq. 2, n=1) by minimizing the difference between $\theta_{app}$ and $\theta_{fit}$, using the modified Hill equation:

$$\theta \text{fit} = \theta \min + (\theta \max - \theta \min) \frac{K_a^n [L]_{tot}^n}{1 + K_a^n [L]_{tot}^n} \quad (2)$$

where $[L_{tot}]$ is the total polyamide concentration, $K_a$ is the equilibrium association constant, and $\theta_{min}$ and $\theta_{max}$ are the experimentally determined site saturation values when the site is unoccupied or saturated, respectively. The data were fit using a nonlinear least-squares fitting procedure of KaleidaGraph software (v. 3.0.1, Abelbeck Software) with $K_a$, $\theta_{max}$, and $\theta_{min}$ as the adjustable parameters. The goodness of fit of the binding curve to the data points is evaluated by the correlation coefficient, with R>0.97 as the criterion for an acceptable fit. All lanes from a gel were used unless a visual inspection revealed a data point to be obviously flawed relative to neighboring points. The data were normalized using the following equation:

$$\theta_{norm} = \frac{\theta_{app} - \theta_{min}}{\theta_{max} - \theta_{min}} \quad (3)$$

Biological Activity

Compounds of this invention were screened for their in vitro activities against different species of bacteria and fungi. Their minimal inhibition concentration (MIC) was determined using the National Committee for Clinical Laboratory Standards (NCCLS) broth microdilution assay in microtiter plates, as set forth in: (1) the guidelines of the National Committee for Clinical Laboratory Standards (NCCLS) Document M7-A4 (NCCLS, 1997); (2) the guidelines of the National Committee for Clinical Laboratory Standards (NCCLS) Document M11-A4 (NCCLS, 1997); and (3) the guidelines and reference method of the National Committee for Clinical Laboratory Standards (NCCLS) Document M27-T (NCCLS, 1995). For antifuingal essays, the method in Murray, P R., 1995 Manual of clinical microbiology (ASM Press, Washington, D.C.), was employed. A variety of Gram-positive and Gram-negative bacteria (aerobes and anaerobes) as well as yeasts and filamentous fungi were tested. These organisms included *Staphylococcus* spp., *Streptococcus* spp., *Enterococcus* spp., *Corynebacterium* spp., *Listeria* spp., *Bacillus* spp., *Micrococcus* spp., *Peptostreptococcus* spp, *Clostridium* spp., *Propionibacterium* spp., *Escherichia* spp., *Pseudomonas* spp., *Haemophilus* spp., *Candida* spp., *Cryptococcus* spp., *Aspergillus* spp., *Trichophyto* spp., *Paecilomyces* spp., *Saccharomyces* spp. and *Fusarium* spp. In addition, effectiveness against some drug resistant microbes were evaluated. Other pathogenic bacteria against which compounds of this invention may be effective include *Acinetobacter* spp., *Alcaligenes* spp., *Campylobacter* spp., *Citrobacter* spp., *Enterobacter* spp., *Proteus* spp., *Salmonella* spp., *Shigella* spp., *Helicobacter* spp., *Neisseria* spp., *Vibrio* spp., *Bacteroides* spp., *Prevotella* spp., *Mycoplasma* spp., *Mycobacteria* spp., and *Clamydia* spp.

Compounds such as V-a, V-b, V-c, V-r, V-s, V-q, V-w, V-x/V-y, V-z/V-aa, V-bb and VIII demonstrated excellent antimicrobial activities against numerous species (Tables I, Ia and II), especially against Gram-positive bacteria and fungi. The MIC's for these compounds were between ≦0.062 μg/mL to >128 μg/mL. One of the most potent compounds, V-a, has MIC's less than 8 μg/mL for most species tested, with the exception of Gram-negative bacteria such as *Escherichia* and *Pseudomonas*. The results indicated that these compounds were broad-spectrum antimicrobial agents. Table Ia and IIa, below, also provides comparative data against the prior art antibiotics distamycin, netropsin, and ofloxacin.

As shown in the preliminary screening, compounds of this invention were active against the isolates resistant to conventional antibiotics, including methicillin resistant staphylococcus aureus, multiple drug resistant *Streptococcus pneumoniae*, vancomycin resistant *Enterococcusfaecium* and polyene resistant *Candida albicans*.

The minimal bactericidal concentration (MBC) has been determined for some of these designed compounds according to NCCLS guideline (Lorian, V. 1996 Antibiotics in laboratory medicine (The Williams & Wilkins Co., Baltimore, Md.)). The difference between the MICs and the MBCs has been established as an index of the bactericidal activity of an antibiotic. The results shown in Table III show that compounds V-a and V-b were microbicidal agents for all species tested.

Compounds of this invention have broad spectrum anti-Gram positive bacteria and antifungal potency. Based on the pattern of antimicrobial activity of these polyamides, the antimicrobial activity should extend into other bacterial and fungal species not listed in the Table I or II. In addition, the compounds have the properties active against the microbes resistant to conventional antibiotics and antifuingal agents. These compounds and their analogs can be used in antimicrobial chemotherapeutics for the treatment of human or animal infections as a systemic and/or topical agent.

In addition to the data presented in the tables below, compounds V-w and V-bb were tested against *Bacillus cereus*, giving MIC's of 0.5 and 8 μg/mL, respectively.

TABLE I

Antibacterial Activity Data

| Organism (ATCC) | Compound (MIC, μg/mL) | | | | | | |
|---|---|---|---|---|---|---|---|
| | V-s | V-a | V-b | V-c | V-q | V-r | VIII |
| Gram-positive bacteria (aerobes) | | | | | | | |
| *Staphylococcus aureus* (29213) | >128 | 2 | 2 | 8 | 8–16 | >128 | 4 |
| *Staphylococcus aureus* (33591) (methicillin resistant) | 64 | 2 | 4 | 16 | 16 | ND | 8 |
| *Staphylococcus epidermidis* (12228) | >128 | 1 | 2 | 8 | 4 | ND | 8 |
| *Enterococcus faecalis* (29212) | 8 | 1 | 1 | 4 | 1 | 16 | 1 |
| *Enterococcus faecium* (51559) (vacomycin resistant) | 128 | 1 | 2–4 | 8 | 4 | ND | 8 |
| *Streptococcus pneumoniae* (49619) | 16 | 0.5 | 0.5 | 2 | 2 | 16 | 1 |
| *Streptococcus pneumoniae* (51422) (multiple drug resistant) | ND | 8 | 1 | 4 | 4 | ND | ND |
| *Streptococcus pyogenes* (49339) | 8 | 0.125 | 0.25 | 2 | 1 | ND | ≦0.062 |
| *Listeria monocytogenes* (19115) | ND | 4 | 8 | ND | ND | ND | 4 |
| *Bacillus anthracis* | ND | 4 | 32 | | ND | ND | ND |
| *Bacillus subtilis* (6633) | 8 | 0.25 | 0.5–1 | 4 | ND | ND | ND |
| *Bacillus cereus* (11778) | 2–4 | 0.25 | 0.5 | 4 | 4–8 | >128 | ND |
| *Micrococcus luteus* (381) | 32 | 2 | 8 | 8 | 8 | ND | ND |
| *Corynebacterium* Group A (49676) | 2–4 | 0.25 | 0.5 | 1 | 1 | ND | 1 |
| Gram-positive bacteria (anaerobes) | | | | | | | |
| *Propionibacterium acnes* (33179) | 16 | 2 | 4 | 8 | ND | ND | ND |
| *Clostridium perfringens* (13124) | 32–64 | 1 | 1 | 2 | ND | ND | ND |
| *Peptostreptococcus asaccharolytics* (29743) | 8 | 0.125 | 0.125 | 0.5 | ND | ND | ND |
| Gram-negative bacteria | | | | | | | |
| *Haemophilus influenzae* (49247) | 64 | 32 | 32 | ND | ND | >128 | ND |
| *Escherichia coli* (25922) | >128 | >128 | >128 | >128 | >128 | >128 | >128 |
| *Pseudomona aeruginosa* (27853) | >128 | >128 | >128 | >128 | >128 | ND | ND |

ND = not determined

TABLE Ia

Additional Antibacterial Activity Data

| ORGANISM (ATCC) | Compound (MIC, μg/mL) * | | | | |
|---|---|---|---|---|---|
| | Distamycin | Netropsin | Ofloxacin | V-x | V-aa |
| Gram-positive bacteria (aerobes) | | | | | |
| *Staphylococcus aureus* (29213) | 32 | 4 | 0.125 | 0.5 | 1 |
| *Staphylococcus aureus* (33591) (MRSA) | 16 | 4 | 0.25 | 1 | 2 |

TABLE Ia-continued

Additional Antibacterial Activity Data

| ORGANISM (ATCC) | Compound (MIC, μg/mL) * | | | | |
|---|---|---|---|---|---|
| | Distamycin | Netropsin | Ofloxacin | V-x | V-aa |
| Staphylococcus epidermidis (12228) | 64 | 2–4 | 0.25 | 0.25 | 0.5–1 |
| Streptococcus pneumoniae (49619) | 16 | 0.125 | 1–2 | 0.125 | 0.25 |
| Streptococcus Group A (49339) | 32 | 8 | 1 | 0.062 | 0.25 |
| Enterococcus faecalis (29212) | 16–32 | 2 | 8 | 0.25 | 1 |
| Enterococcus faecium (51559) (VREF) | 128 | 8 | 8 | 0.25 | 1 |
| Listeria monocytogenes (19115) | ND | ND | 1 | 0.25 | 0.5 |
| Corynebacterium Group A (49676) | 16 | 0.5 | 0.125 | 0.125 | 0.25 |
| Micrococcus luteus (381) | 32 | ND | 1 | 1 | 1 |
| Bacillus subtilis (6633) | 64–128 | 4 | 0.125 | 0.25 | 0.5 |
| Bacillus cereus (11778) | 8 | 2 | 0.125 | 0.25 | 0.5 |
| Gram-positive bacteria (anaerobes) | | | | | |
| Propionibacterium acnes (33179) | 16 | ND | 0.25 | ND | ND |
| Clostridium perfringens (13124) | 8 | ND | 0.25 | ND | ND |
| Peptostreptococcus asaccharolytics (29743-1) | 8 | ND | 0.5 | ND | ND |
| Gram-negative bacteria | | | | | |
| Haemophilus influenzae | ND | 4 | 0.25 | ND | ND |
| Escherichia coli (25922) | >128 | 2 | 0.03 | >128 | >128 |
| Pseudomona aeruginosa (27853) | >128 | >128 | >128 | ND | ND |

ND = Not determined
* Data for distamycin, netropsin, and ofloxacin is comparative data.

TABLE II

Antifungal Activity

| Organism (ATCC) | Compound (MIC, μg/mL) | | | | | | |
|---|---|---|---|---|---|---|---|
| | V-s | V-a | V-b | V-c | V-q | V-r | VIII |
| Yeasts | | | | | | | |
| Candida albicans (90028) | >128 | 4 | 4 | 8 | ND | >128 | ND |
| Candida albicans (38247) (Polyene resistant) | ND | 4 | ND | ND | ND | >128 | ND |
| Candida tropicalis (13803) | ND | ND | ND | ND | ND | ND | 2 |
| Candida parasilosis (10232) | ND | ND | ND | ND | ND | 2 | 128 |
| Cryptcoccus neoformans (90112) | ND | ND | ND | ND | ND | 16 | 16 |
| Saccharomyces cerevisiae (44773) | ND | 8 | ND | ND | ND | ND | ND |
| Filamentous fungi | | | | | | | |
| Aspergillus niger (10535) | ND | 2 | 4 | ND | ND | ND | ND |
| Fusarium solani (36031) | ND | 4 | 4–8 | ND | ND | ND | ND |
| Paecilomyces variotii (22319) | ND | 0.5 | 0.5 | ND | ND | ND | ND |
| Trichophyto tonsurans (28942) | ND | 16 | 16 | ND | ND | ND | ND |

ND = not determined

TABLE IIa

Additional Antifungal Activity Data

| ORGANISM (ATCC) | Compound (MIC, μg/mL) * | | | | |
|---|---|---|---|---|---|
| | Distamycin | Netropsin | Ofloxacin | V-x | V-aa |
| Yeasts | | | | | |
| Candida albicans (90028) | >128 | ND | ND | ND | ND |
| Candida albicans (38247) | >128 | ND | ND | 4 | 16 |

TABLE IIa-continued

Additional Antifungal Activity Data

Compound (MIC, µg/mL) *

| ORGANISM (ATCC) | Dista-mycin | Netrop-sin | Ofloxacin | V-x | V-aa |
|---|---|---|---|---|---|
| Candida tropicalis (13803) | >128 | 16 | ND | 2 | 4 |
| Candida parapsilosis (10232) | >128 | 16 | ND | 2 | 4 |
| Cryptococcus neoformans (90112) | >128 | 4 | ND | 2 | 4 |

ND = Not determined
* Data for distamycin, netropsin, and ofloxacin is comparative data.

TABLE III

Microbiocidal Activity

| | Compound | | | |
|---|---|---|---|---|
| | V-a (µg/mL) | | V-b (µg/mL) | |
| ORGANISM (ATCC) | MIC | MBC | MIC | MBC |
| Staphylococcus aureus (29213) | 2 | 2 | 2 | 4 |
| Staphylococcus aureus (33591) (methicillin resistant) | 2 | 4 | 4 | ND |
| Staphylococcus epidermidis (12228) | 1 | 1 | 2 | ND |
| Enterococcus faecalis (29212) | 1 | >4 | 1 | >4 |
| Enterococcus faecium (51559) (vacomycin resistant) | 1 | 2–4 | 2–4 | ND |
| Streptococcus pneumoniae (49619) | 0.5 | 0.5 | 0.5 | 0.5 |
| Streptococcus pyogenes (49339) | 0.125 | 0.125 | 0.25 | ND |
| Bacillus subtilis (6633) | 0.25–0.5 | 0.5 | 0.5–1 | ND |
| Bacillus cereus (11778) | 0.25 | 0.5 | 0.5 | 0.5 |
| Micrococcus luteus (381) | 0.25–0.5 | 0.5 | 0.5–1 | ND |
| Corynebacterium Group A (49676) | 0.25–0.5 | 0.25 | 0.5 | ND |
| Propionibacterium acnes (33179) | 4 | 8 | 4 | ND |
| Clostridium perfringens (13124) | 1 | 2 | 1 | ND |
| Peptostreptococcus asaccharolytics (29743) | 0.125 | 0.25 | 0.125 | ND |
| Candida albicans (90028) | 4 | 4 | 4 | 4 |

TABLE III-continued

Microbiocidal Activity

| | Compound | | | |
|---|---|---|---|---|
| | V-a (µg/mL) | | V-b (µg/mL) | |
| ORGANISM (ATCC) | MIC | MBC | MIC | MBC |
| Saccharomyces cerevisiae (44773) | 8 | 8 | 16 | 16 |

ND = not determined
Additional illustrative biological activity data is shown in Table IV:

TABLE IV

| | MIC, µg/mL | | | |
|---|---|---|---|---|
| Compound | S. aureus (29213) | B. cereus (11778) | E. coli (25922) | C. albicans (38247) |
| V-x | 0.5, 1 | 0.25, 2 | 32, 128 | 4, 8 |
| V-z | 1 | 0.5 | 128 | 16 |
| V-dd | 1 | 1 | 128 | 4 |
| V-ee | 0.25, 0.125 | 0.25 | 64, 32 | 2 |
| V-ff | 1 | 2 | 32 | 16 |
| V-gg | 2, 1 | 2, 0.5 | 32 | 32 |
| V-hh | 1 | 1 | 32 | 32 |
| V-ii | 1 | 1 | 32 | 2 |
| V-jj | 0.5 | 0.25 | 32 | 1 |
| V-kk | 0.5 | 0.25 | 32 | 0.25 |
| V-ll | 0.25 | 0.5 | 32 | 4 |
| V-mm | 0.5 | 0.25 | 32 | 32 |
| V-nn | 0.031 | 0.064 | 32 | 1 |
| V-oo | 0.25 | 0.5 | 32 | 1 |
| V-pp | 0.5 | 0.5 | 32 | 4 |
| V-qq | 0.25 | 0.25 | 32 | 32 |
| V-rr | 1 | 0.5 | 32 | 32 |
| V-tt | 0.5 | 0.25 | 32 | 32 |
| V-uu | 0.25 | 1 | 4, 32 | 32, 4 |

The foregoing detailed description of the invention includes passages that are chiefly or exclusively concerned with particular parts or aspects of the invention. It is to be understood that this is for-clarity and convenience, that a particular feature may be relevant in more than just the passage in which it is disclosed, and that the disclosure herein includes all the appropriate combinations of information found in the different passages. Similarly, although the various descriptions herein relate to specific embodiments of the invention, it is to be understood that where a specific feature is disclosed in the context of a particular embodiment, such feature can also be used, to the extent appropriate, in the context of another figure or embodiment, in combination with another feature, or in the invention in general.

Further, while the present invention has been particularly described in terms of certain preferred embodiments, the invention is not limited to such preferred embodiments. Rather, the scope of the invention is defined by the appended claims.

What is claimed is:

1. A charged compound represented by the formula (VI):

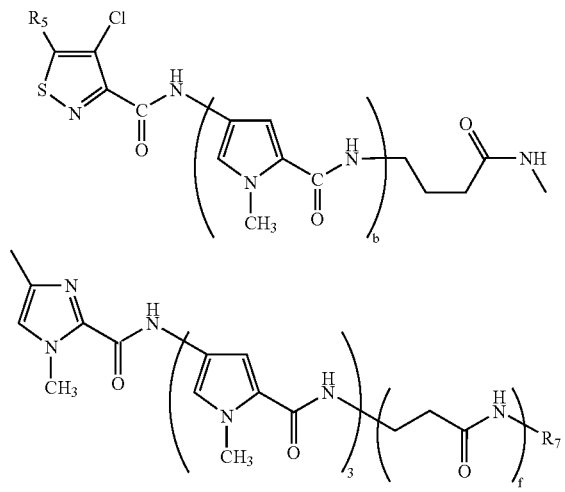

wherein
R$_5$ is a member selected from the group consisting of halogen, OR$_7$ and N(R$_7$)$_2$;
each R$_7$ is independently selected from the group consisting of H, a substituted or unsubstituted (C$_1$-C$_{12}$) alkyl group and a substituted or unsubstituted (C$_1$-C$_{12}$)heteroalkyl group;
b is 1, 2, 3 or 4; and
f is 0 or 1;
with the proviso that at least one of R$_5$ and R$_7$ is a positively charged group.

2. A charged compound according to claim 1, wherein f is 1.

3. A charged compound according to claim 1, wherein R$_5$ is Cl.

4. A charged compound according to claim 1, wherein R$_5$ is a positively charged group.

5. A charged compound according to claim 1, wherein R$_7$ is a positively charged group.

6. A charged compound according to claim 1, wherein R$_5$ and R$_7$ both are a positively charged groups.

7. A charged compound according to claim 1, wherein R$_5$ is selected from the group consisting of:

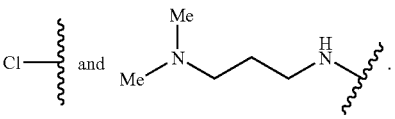

8. A charged compound according to claim 1, wherein R$_7$ is

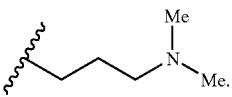

9. A composition comprising a pharmaceutically acceptable carrier and an anti-infective amount of a compound of claim 1.

10. A method of inhibiting pathogen proliferation, comprising contacting a pathogen of a eukaryotic organism with a proliferation-inhibiting amount of a compound of claim 1.

11. A method according to claim 10 wherein the pathogen is selected from the group consisting of *Staphylococcus* spp., *Streptococcus* spp., *Enterococcus* spp., *Corynebacterium* spp., *Listeria* spp., *Bacillus* spp., *Micrococcus* spp., *Peptostreptococcus* spp, *Clostridium* spp., *Propionibacterium* spp., *Escherichia* spp., *Pseudomonas* spp., *Haemophilus* spp., *Candida* spp., *Cryptococcus* spp., *Aspergillus* spp., *Trichophyto* spp., *Paecilomyces* spp., *Saccharomyces* spp., *Fusarium* spp., *Acinetobacter* spp., *Alcaligenes* spp., *Campylobacter* spp., *Citrobacter* spp., *Enterobacter* spp., *Proteus* spp., *Salmonella* spp., *Shigella* spp., *Helicobacter* spp., *Neisseria* spp., *Vibrio* spp., *Bacteroides* spp., *Prevotella* spp., *Mycoplasma* spp., *Mycobacteria* spp., and *Clamydia* spp.

* * * * *

SEQUENCE LISTING

<160> NUMBER OF SEQ ID NOS: 1

<210> SEQ ID NO 1
<211> LENGTH: 92
<212> TYPE: DNA
<213> ORGANISM: Artificial Sequence
<220> FEATURE:
<223> OTHER INFORMATION: Description of Artificial Sequence:partial
      nucleotide sequence of dsDNA restriction fragment
      used for footprinting experiments

<400> SEQUENCE: 1
ctagatgccg ctaagtacta tgccgctaac tactatgccg ctaattacta tgccgctaaa    60
tactatgccg ctaactagta tgccgctatg ca                                  92